United States Patent
Lao et al.

(10) Patent No.: US 10,149,920 B2
(45) Date of Patent: *Dec. 11, 2018

(54) IMPLANT WITH CONTROLLED POROSITY MADE OF A HYBRID MATERIAL

(71) Applicants: UNIVERSITE BLAISE PASCAL-CLERMONT-FERRAND II, Clermont-Ferrand (FR); CENTRE NATIONAL DE LA RECHERCHE SCIENTIFIQUE, Paris (FR)

(72) Inventors: Jonathan Claude Alexandre Lao, Veyre-Monton (FR); Joséphine Lacroix, Clermont-Ferrand (FR); Edouard Daniel Albert Jallot, Saint-Beauzire (FR); Xavier Dieudonne, Ceyrat (FR)

(73) Assignees: UNIVERSITE CLERMONT AUVERGNE, Clermont Ferrand (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/894,943

(22) PCT Filed: Jun. 3, 2014

(86) PCT No.: PCT/IB2014/061914
§ 371 (c)(1),
(2) Date: Dec. 30, 2015

(87) PCT Pub. No.: WO2014/195863
PCT Pub. Date: Dec. 11, 2014

(65) Prior Publication Data
US 2016/0114076 A1 Apr. 28, 2016

(30) Foreign Application Priority Data

Jun. 3, 2013 (FR) ..................... 13 55057

(51) Int. Cl.
*A61L 27/10* (2006.01)
*A61L 27/18* (2006.01)
(Continued)

(52) U.S. Cl.
CPC ............... *A61L 27/10* (2013.01); *A61L 27/16* (2013.01); *A61L 27/18* (2013.01); *A61L 27/20* (2013.01);
(Continued)

(58) Field of Classification Search
CPC ...... A61L 27/16; A61L 2420/02; A61L 27/20; A61L 27/306; A61L 27/446
See application file for complete search history.

(56) References Cited

U.S. PATENT DOCUMENTS

2004/0052861 A1* 3/2004 Hatcher ................ A61L 27/446
424/602
2011/0009327 A1* 1/2011 Hill ....................... A61L 27/427
514/16.7

OTHER PUBLICATIONS

Draghi et al., "Microspheres leaching for scaffold porosity Control", Journal of Materials Science: Materials in Medicine 2005 16:1093-1097.*
(Continued)

*Primary Examiner* — Jianfeng Song
(74) *Attorney, Agent, or Firm* — Christensen O'Connor Johnson Kindness PLLC

(57) ABSTRACT

The disclosure relates to an implant material for filling bone defects, for bone regeneration, and for bone tissue engineering, to an implant comprising this material, to a method for producing such an implant, and to a method for producing a hybrid material. The implant material comprises a hybrid material comprising: a bioactive glass M based on $SiO_2$ and CaO, optionally containing $P_2O_5$ and/or optionally doped with strontium, and a biodegradable polymer P soluble in a (Continued)

solvent and chosen from among bioresorbable polysaccharides. The implant material has applications in the medical field.

13 Claims, 12 Drawing Sheets

(51) Int. Cl.
  *A61L 27/20*  (2006.01)
  *A61L 27/58*  (2006.01)
  *A61L 27/16*  (2006.01)
  *A61L 27/54*  (2006.01)
  *A61L 27/56*  (2006.01)
  *A61L 27/22*  (2006.01)
  *A61L 27/24*  (2006.01)
  *A61L 27/30*  (2006.01)
  *A61L 27/44*  (2006.01)

(52) U.S. Cl.
  CPC ............. *A61L 27/222* (2013.01); *A61L 27/24* (2013.01); *A61L 27/306* (2013.01); *A61L 27/446* (2013.01); *A61L 27/54* (2013.01); *A61L 27/56* (2013.01); *A61L 27/58* (2013.01); *A61L 2300/102* (2013.01); *A61L 2300/412* (2013.01); *A61L 2420/02* (2013.01); *A61L 2430/02* (2013.01)

(56) References Cited

OTHER PUBLICATIONS

Pereira et al., "Preparation of bioactive glass-polyvinyl alcohol hybrid foams by the sol-gel method", Journal of Materials Science: Materials in Medicine 16 (2005) 1045-1050.*

Written Opinion of the International Searching Authority dated Aug. 8, 2014, issued in corresponding International Application No. PCT/IB2014/061914, filed Jun. 3, 2014, 7 pages.

International Preliminary Report on Patentability dated Dec. 8, 2015, issued in corresponding International Application No. PCT/IB2014/061914, filed Jun. 3, 2014, 1 page.

Hafezi, F., et al., "Transplantation of Nano-Bioglass/Gelatin Scaffold in a Non-Autogenous Setting for Bone Regeneration in a Rabbit Ulna," Journal of Materials Science: Materials in Medicine 23(11):2783-2792, Nov. 2012.

Rodenas-Rochina, J., et al., "Comparative Study of PCL-HAp and PCL-Bioglass Composite Scaffolds for Bone Tissue Engineering," Journal of Materials Science: Materials in Medicine 24(5):1293-1308, May 2013.

International Search Report dated Aug. 8, 2014, issued in corresponding International Application No. PCT/IB2014/061914, filed Jun. 3, 2014, 5 pages.

Blaker, J.J., et al., "Mechanical properties of highly porous PDLLA/Bioglass® composite foams as scaffolds for bone tissue engineering," Acta Biomaterialia, Nov. 2005, 1, 643-652.

Hench, L.L., et al., "Bonding Mechanisms at the Interface of Ceramic Prosthetic Materials," J. Biomed. Mater. Res., Nov. 1971, 2, 117-141.

Hench, L.L., et al., "Direct Chemical Bond of Bioactive Glass-Ceramic Materials to Bone and Muscle," J. Biomed. Mater. Res., May 1973, 4, 25-42.

Descamps, M. et al., "Synthesis of macroporous beta-tricalcium phosphate with controlled porous architectural," Ceramics International, Jul. 2008, 34, (5), 1131-1137.

Kim, H., et al. "Hydroxyapatite and gelatin composite foams processed via novel freeze-drying and crosslinking for use as temporary hard tissue scaffolds," J. Biomed. Mater. Res. 72A: 136-145, Feb. 2005.

Vallet-Regi, M. et al., "Glasses with Medical Applications," Eur. J. Inorg. Chem., Mar. 2003, 1029-1042.

Karageorgiou, V. et al., "Porosity of 3D biomaterial scaffolds and osteogenesis," Biomaterials, Sep. 2005, 26, 5474-5491.

Lin, S., et al., "Nanostructure evolution and calcium distribution in sol-gel derived bioactive glass," Journal of Materials Chemistry, Jan. 2009, 19, 1276-1282.

Descamps, M., et al., "Manufacture of macroporous beta-tricalcium phosphate bioceramics," Journal of the European Ceramic Society, Jan. 2008, 28, (1), 149-157.

* cited by examiner

IMPLANT WITH CONTROLLED POROSITY MADE OF A HYBRID MATERIAL

The invention relates to an implant material for filling bone defects, for bone regeneration and for bone tissue engineering, an implant comprising said material, a method for manufacturing such an implant as well as a method for manufacturing a hybrid material.

The overall aging of the population and the disorders of the osteoarticular system that accompany this make it necessary to develop high-performance materials for replacing bone tissues. 18 billion Euros of health care costs are in fact expended each year in France for diseases of the osteoarticular system and dental diseases; musculoskeletal disorders are the commonest occupational pathologies in the industrialized countries, whereas osteoporosis develops in elderly patients; these facts delineate the contours of a major societal and economic challenge and explain the increasing demand for biomaterials, implants with increased lifetimes capable of making up for bone loss.

As recourse to grafts is limited, and materials of animal origin may pose problems of biocompatibility or risks of infection, research efforts aim to develop synthetic biomaterials capable of promoting bone regeneration.

In this case they are called bioactive implants: the material implanted is not simply intended to make up for bone loss passively, remaining as inert as possible, but on the contrary it has to stimulate and participate actively in the mechanism of bone regeneration. This is particularly important in the case of extensive bone defects, for which the self-repair mechanism no longer functions.

Currently the main bioactive materials used as bone substitutes are the bioactive "ceramics", such as the calcium phosphates, and the bioactive glasses, also called "bioglasses".

The first bioactive ceramics were developed by L. L. Hench (L. L. Hench et al., J. Biomed. Mater. Res. 1971, 2, 117-141; L. L. Hench et al., J. Biomed. Mater. Res. 1973, 7, 25-42).

The first bioactive glasses were prepared from $SiO_2$, $P_2O_5$, CaO and $Na_2O$. The oxides of silicon and of phosphorus are network formers that participate in the cohesion of the vitreous network. The alkali and alkaline-earth metals such as sodium and calcium do not display this capacity and modify the vitreous network by introducing chain breaks in it, which are the cause of the low melting point of these glasses, associated with increased structural disorder. Their presence results in greater reactivity of the bioactive glasses notably through their corrosion in an aqueous environment. This reactivity allows formation of hydroxyapatite in the physiological medium and therefore promotes bone reconstruction.

The bioglass that has received the most study is a soda-silico-phospho-calcium glass called Bioglass® or Hench Bioglass. Its basic composition is 45% $SiO_2$-24.5% CaO-24.5% $Na_2O$-6% $P_2O_5$, by weight relative to the total weight of the composition. The remarkable bioactive properties of this material require no further demonstration. Bioglass® is still one of the most interesting bioactive materials (inducing a specific response from the cells).

There have been numerous developments in the field of bioactive glasses since their discovery (M. Vallet-Regi et al., Eur. J. Inorg. Chem. 2003, 1029-1042), such as the incorporation of various atoms or the incorporation of active principles. The compositions of the bioactive glasses have been optimized so as to promote the proliferation of osteoblasts and the formation of bone tissues (WO 02/04606).

Incorporation of silver has been proposed notably for endowing bioactive glasses with antibacterial properties (WO 00/76486).

In its turn, application WO 2009/027594 describes a bioactive glass in which strontium is introduced in amounts between 0.1 and 10% of the total weight of the bioactive glass.

A characteristic feature of these bioactive materials is that they are simultaneously biocompatible, capable of binding spontaneously to bone tissues, of promoting adhesion of bone cells and, finally, of being bioabsorbable, being gradually replaced with newly formed bone tissue as bone regrowth progresses.

However, despite this very satisfactory set of characteristics, the fragility of these materials limits their applications: in fact, although their rigidity is often greater than that of bone, their lack of flexibility and toughness means that the bioactive materials cannot be implanted in mechanically loaded sites.

To overcome this defect, an ingenious solution is to take inspiration from the particular structure of bone tissue. It is complex, consisting mainly of a composite weft intimately mixed with an inorganic phase, the bone mineral consisting of crystals of apatite (absorbable calcium phosphate), with an organic phase, which is predominantly collagen. Remarkably, this composite structure combines the initial rigidity of the inorganic part with the natural toughness and flexibility of the collagen fibers. To obtain implants with mechanical properties close to bone tissue, one strategy therefore consists of combining bioactive materials and biodegradable polymers within one and the same composite or hybrid matrix.

For filling extensive bone defects, in addition to the above characteristics, the implants must have a specific morphology: the latter takes inspiration from trabecular bone, namely a highly porous structure consisting of a three-dimensional network of interconnected macropores of several hundreds of microns. In fact, in the case of extensive bone defects, the bone cells need an extracellular "support" matrix capable of guiding and stimulating cellular adhesion, proliferation, and differentiation, while being compatible with the processes of vascularization and tissue invasion.

This macroporous structure is also required for the new applications envisaged in bone tissue engineering: it is a matter of manufacturing in the laboratory, starting from cells taken from the patient, new bone tissue that can later be re-implanted in the patient. For optimal tissue culture, it must also be supported on porous three-dimensional supports allowing good cellular adhesion, differentiation into mature cells as well as production of tissue and in particular biomineralization.

To summarize, although numerous materials and formulations have been developed for making up for bone loss, none fully meets the specifications describing an ideal implant, namely it should:
  be biocompatible;
  be bioactive: spontaneously induce the formation of a strong interfacial bond with the bone tissues, promote adhesion and cellular activity;
  be bioabsorbable;
  have a suitable morphology based on a three-dimensional matrix of interconnected macropores;
  have good mechanical behavior;
  be derived from a method of manufacture allowing easy and sufficiently flexible forming for adapting to the numerous geometries of defects.

"Suitable morphology based on a three-dimensional matrix of interconnected macropores" means that the size, shape and distribution of the pores as well as the size of the interconnections between these pores must be controlled.

The aim of the invention is to propose a material that responds perfectly to all these criteria and that can be manufactured by a method that allows the production of porous architectures made up of an inorganic part and an organic part, in the form of a hybrid material, in contrast to the methods of the prior art.

For this purpose, the invention proposes a method for manufacturing an implant made of a hybrid material for filling bone defects, for bone regeneration and for bone tissue engineering, characterized in that it comprises the following steps:

a) selecting a bioactive glass M based on $SiO_2$ and CaO, optionally containing $P_2O_5$ and/or optionally doped with strontium, b) selecting a biodegradable polymer P that is soluble in at least one solvent S1 and insoluble in at least one solvent S different from the solvent S1, c) selecting microspheres of a porogenic agent A having diameters and sizes corresponding to the desired diameters and sizes of the pores in the material constituting the implant to be manufactured, this porogenic agent A being:
  of a polymer insoluble in the at least one solvent S1 and soluble in the at least one solvent S,
  the at least one solvent S in which the material of the biodegradable polymer P is insoluble and the at least one solvent S in which the material of the porogenic agent A is soluble being identical, d) putting at least 60 vol %, preferably 70 vol % relative to the total volume of the mixture of porogenic agent A-biodegradable polymer P-alkoxide precursors of the bioactive glass M, of microspheres of the porogenic agent A in a mold having the required shape and size for the implant, these microspheres forming a compact stack corresponding to the shape and size of the pores to be obtained in the implant material, e) adding the biodegradable polymer P to the alkoxide precursors of the bioactive glass M and homogenizing the mixture, f) putting the mixture obtained in step e) into the mold, g) gelling the mixture contained in the mold after step f), h) removing the mixture obtained in step g) from the mold, i) removing the microspheres of porogenic agent A by washing with the solvent S.

In a first embodiment of the method of the invention, step e) and/or step f) are carried out before step d).

In a second embodiment of the method of the invention, steps d) and e) and f) are carried out simultaneously.

In all the embodiments, the method of the invention may further comprise a step j) of crosslinking of the material obtained in step i).

Moreover, in all the embodiments of the method of the invention, the biodegradable polymer P is selected from:
  biodegradable polymers that are soluble in at least one solvent S1 and insoluble in at least one solvent S selected from:
    bioabsorbable polysaccharides, preferably selected from dextran, hyaluronic acid, agar, chitosan, alginic acid, sodium or potassium alginate, galactomannan, carrageenan, pectin,
    bioabsorbable polyesters, preferably polyvinyl alcohol (PVA) or poly(lactic acid) (PLA),
    biodegradable synthetic polymers, preferably a polyethylene glycol (PEG), or poly(caprolactone) (PCL),
    proteins, preferably gelatin or collagen,
  and the material of the porogenic agent A is selected from biodegradable polymers that are insoluble in the at least one solvent S1 and soluble in the at least one solvent S, preferably selected from $C_1$ to $C_4$ polyalkyl methacrylates, preferably polymethyl methacrylate or polybutyl methacrylate, polyurethane, polyglycolic acid, the various forms of polylactic acids, the copolymers of lactic-coglycolic acids, polycaprolactone, polypropylene fumarate, paraffin and naphthalene, acrylonitrile butadiene styrene (ABS),
  the material of the porogenic agent A being different from the biodegradable polymer P.

Preferably, the weight ratio biodegradable polymer P/bioactive glass M is between 10/90 and 90/10, preferably, for reasons of mechanical behavior of the material obtained, it will be between 20/80 and 80/20, the best mechanical behavior (easy manipulation without distortion or loss of material) being obtained with a 70/30 ratio.

Also preferably, the bioactive glass M is a glass based on $SiO_2$ and CaO, the biodegradable polymer P is gelatin, the material of the microspheres of porogenic agent A is polymethyl methacrylate and the solvent S is acetone.

The method of the invention may further comprise, in step f), a step of introducing a coupling agent, preferably an organoalkoxysilane compound, more preferably 3-glycidoxypropyltrimethoxysilane (GPTMS), even more preferably 3-glycidoxypropyltriethoxysilane (GPTES).

It may also further comprise, after step d), a step of enlarging the interconnections, by infiltration of a solvent S of the material of the porogenic agent A, in the stack of the microspheres of porogenic agent A and/or by heating this stack.

The invention also proposes a method for manufacturing a hybrid material comprising a biodegradable polymer P and a bioactive glass M based on $SiO_2$ and CaO and optionally containing $P_2O_5$ and/or optionally doped with strontium, characterized in that it comprises the following steps:

A) preparing a sol of the alkoxide precursors of a bioactive glass M based on $SiO_2$ and CaO, optionally containing $P_2O_5$ and/or optionally doped with strontium, B) adding a solution containing the biodegradable polymer P, dissolved in a solvent S1, to the sol in step A), C) sol-gel polymerization of the alkoxide precursors and gelation of the mixture obtained in step B) at a temperature between 0° C. and 60° C., under air.

The invention further proposes an implant material for filling bone defects, for bone regeneration and for bone tissue engineering,
  characterized in that it comprises a hybrid material comprising:
    a bioactive glass M based on $SiO_2$ and CaO, optionally containing $P_2O_5$ and/or optionally doped with strontium, and
    a biodegradable polymer P soluble in the at least one solvent S1 selected from:
      bioabsorbable polysaccharides, preferably selected from dextran, hyaluronic acid, agar, chitosan, alginic acid, sodium or potassium alginate, galactomannan, carrageenan, pectin,
      bioabsorbable polyesters, preferably polyvinyl alcohol or poly(lactic acid),
      biodegradable synthetic polymers, preferably a polyethylene glycol, or poly(caprolactone), and
      proteins, preferably gelatin or collagen, and in that it consists of a matrix comprising the hybrid material, said matrix having at least 70% by number of pores having the shape of spheres or of spherical polyhedra inscribed within a sphere, the diameter of the spheres being between 100 and 900 µm, preferably between 200 and 800 µm inclusive, with a difference between the diameter of the smallest or the largest sphere being at most 70%, preferably at most 50%, more preferably at most 30%, relative to the arithmetic mean diameter of the set of spheres of the implant and the interconnections between the pores having their smallest dimension between 25 µm and 250 µm inclusive, at least 70% by number of these pores having at least one interconnection with another pore.

The invention finally proposes an implant for filling bone defects, for bone regeneration and for bone tissue engineering, characterized in that it comprises a material according to the invention or obtained by the method for manufacturing an implant according to the invention.

The invention will be better understood and other features and advantages of the invention will become clearer on reading the explanatory description that follows, which refers to the appended figures in which:

FIG. 1 shows a sectional view taken with the scanning electron microscope, of the implant made of composite material obtained in example 1, at a magnification of ×70, FIG. 2 is a schematic representation of the implant material according to the invention, FIG. 3 shows a photograph, taken with a scanning electron microscope, of the implant obtained in example 3, the matrix of which consists of gelatin covered with a bioactive glass, at a magnification of ×100, FIG. 4 shows a photograph, taken with a scanning electron microscope, at a magnification of ×50, of a section of an implant material of the prior art prepared by a lyophilization method, described in Kim et al. "Hydroxyapatite and gelatin composite foams processed via novel freeze-drying and crosslinking for use as temporary hard tissue scaffolds" J Biomed Mater Res 72A: 136-145, 2005, FIG. 5 shows a photograph, taken with a scanning electron microscope, at a magnification of ×200, of an implant material of the prior art prepared by a method of thermally induced phase separation, described in Blaker et al. "Mechanical properties of highly porous PDLLA/Bioglass® composite foams as scaffolds for bone tissue engineering" Acta Biomater 2005, 1, 643-52, FIG. 6 shows a photograph taken, with a scanning electron microscope, at a magnification of ×50, of a hybrid implant material according to the invention with gelatin/glass weight ratio of 70/30, obtained by the method of the invention comprising a step of increasing the size of the interconnections between pores by infiltration with an acetone-ethanol mixture at 30 vol % of acetone, relative to the total volume of the mixture for 5 minutes by infiltration with the mixture in the stack of microspheres of porogenic agent, alone, FIG. 7 is a photograph, taken with a scanning electron microscope, at a magnification of ×50, of the same implant material according to the invention as shown in FIG. 6 but after infiltration with an acetone-ethanol mixture at 30 vol % of acetone, relative to the total volume of the mixture, for 15 minutes, with the mixture in the stack of microspheres of porogenic agent, alone, FIG. 8 is a photograph, taken with a scanning electron microscope, at a magnification of ×50, of the material shown in FIG. 6 and FIG. 7 obtained by the method of the invention after increasing the size of the interconnections between pores by infiltration of the acetone-ethanol mixture at 30 vol % of acetone, relative to the total volume of the mixture, for 30 minutes, with the mixture in the stack of microspheres of porogenic agent, alone, FIG. 9 is a curve representing the increase in the size of the interconnections between pores by infiltration with an acetone-ethanol mixture at 30 vol % of acetone, relative to the total volume of the mixture, as a function of the infiltration time, FIG. 10 is a photograph, taken with a scanning electron microscope, at a magnification of ×100, of a hybrid implant material according to the invention consisting of 70% of gelatin and 30% of glass, by weight, according to the invention obtained by the method of the invention after increasing the size of the interconnections of the pores by heating the stack of microspheres of porogenic agent, alone, at 125° C. for 15 minutes, under air, FIG. 11 is a photograph, taken with a scanning electron microscope, at a magnification of ×100, of the implant material shown in FIG. 10 but after increasing the size of the interconnections of pores by heating the stack of microspheres of porogenic agent, alone, at 125° C. for 1 hour, before infiltration with the hybrid material consisting of 70% of gelatin and 30% of glass, by weight, FIG. 12 is a photograph, taken with a scanning electron microscope, at a magnification of ×100, of the same composition of the implant material according to the invention as shown in FIGS. 10 and 11, obtained by the method of the invention after increasing the size of the interconnections of pores by heating the stack of microspheres of porogenic agent, alone, at 125° C., for 2 hours, FIG. 13 shows the curve of the variation in size of the interconnections between pores as a function of the time of heating the stack of microspheres of porogenic agent, alone, at 125° C., FIG. 14A is a photograph, taken with a scanning electron microscope, at a magnification of ×100, of the hybrid material obtained in example 16, FIG. 14B shows the PIXE (Particles or Protons Induced X-ray Emission) spectrum of the hybrid material obtained in example 16, FIG. 15 is a photograph, taken with a scanning electron microscope, at a magnification of ×100, of the hybrid material according to the invention obtained in example 7, FIG. 16 is a photograph, taken with a scanning electron microscope, at a magnification of ×100, of the implant material according to the invention obtained in example 8, FIG. 17 is a photograph, taken with a scanning electron microscope, at a magnification of ×30, of the implant material according to the invention obtained in example 9, FIG. 18 is a photograph, taken with a scanning electron microscope, at a magnification of ×100, of the implant material according to the invention obtained in example 10, FIG. 19 is a photograph, taken with a scanning electron microscope, at a magnification of ×70, of the implant material according to the invention obtained in example 11, FIG. 20 is a photograph, taken with a scanning electron microscope, at a magnification of ×30, of the implant material according to the invention obtained in example 12, FIG. 21 is a photograph, taken with a scanning electron microscope, at a magnification of ×70, of the implant material according to the invention obtained in example 13, and FIG. 22 is a photograph, taken with a scanning electron microscope, at a magnification of ×30, of the implant material according to the invention obtained in example 14.

Throughout this text, the following terms have the following definitions:

"interconnection(s) between pores": opening(s) allowing passage from one pore to another, "aqueous medium": any liquid medium containing water, or water alone, "biodegradable": degradable in a physiological fluid, for example a buffered saline solution (SBF), "bioabsorbable": removable from a physiological medium containing biological cells, "arithmetic mean diameter of the set of pores": sum of the diameters of the pores/number of pores, "spherical pore" or "sphere": pore or sphere for which the ratio of the smallest diameter to the largest diameter is 0.9±0.1, "polyhedron inscribed in a sphere": polyhedron inscribed in a sphere having the same diameter at all points, the differences between the different diameters of the polyhedron inscribed in this sphere being at most ±15% of the diameter of the sphere in which they are inscribed, "compact stack of microspheres of porogenic agent A": stack of microspheres of porogenic agent A in which:
at least 70% by number, preferably more than 95% by number of microspheres are in contact with one another, and remain in contact with one another when the mixture porogenic agent A and biodegradable hybrid polymer P-bioactive glass M is in the mold, and when the stack of microspheres is covered and infiltrated with the bioactive glass M-biodegradable polymer P hybrid mixture.

Said compact stack of microspheres of porogenic agent A may be obtained by centrifugation of the mixture of microspheres of porogenic agent A and biodegradable hybrid polymer P-bioactive glass M or else by applying a negative pressure (vacuum) or positive pressure (above atmospheric pressure) on the mixture of microspheres of porogenic agent A and biodegradable hybrid polymer P-bioactive glass M introduced into the mold, before and during gelation of this mixture.

The implant material for filling bone defects, for bone regeneration and for bone tissue engineering will be described with reference to FIGS. 1 and 2.

As can be seen in FIGS. 1 and 2, the implant material of the invention comprises a matrix, designated 1 in FIGS. 1 and 2, of a material that comprises an organic part and an inorganic part.

This material is biocompatible, bioactive, bioabsorbable and, as can be seen in FIGS. 1 to 3, it has a very regular morphology, in terms of pore distribution and in terms of pore shape, in contrast to the materials of the prior art, which have a chaotic pore distribution, size and shape, as can be seen in FIGS. 4 and 5, which show respectively photographs taken with the scanning electron microscope, of implant materials obtained by a lyophilization method (FIG. 4) and a method of thermally induced phase separation (FIG. 5).

In particular, this material has pores, designated 2 in FIGS. 1 to 3, in the form of spheres whose diameter, designated 3 in FIG. 2, either is identical at all points, or in the form of spheres whose ratio of the smallest diameter to the largest diameter is 0.9±0.1, as a maximum, or in the form of polyhedra inscribed in such a sphere, the differences between the diameters at different points of the polyhedron inscribed in this sphere being at most approximately 15% of the diameter of the sphere in which they are inscribed.

The implant materials of the invention may have pore sizes that are in a very wide range from 100 to 900 µm, preferably 200 µm to 800 µm inclusive, with a difference between the diameter of the smallest or the largest sphere being at most 70%, preferably at most 50%, more preferably at most 30%, relative to the arithmetic mean diameter of the set of spheres of the implant in association with the interconnections, designated 4 in FIGS. 1 to 3, between pores whose smallest dimension is between 25 µm and 250 µm, inclusive.

At least 70% by number of these pores have at least one interconnection with another pore.

Thus, this form and distribution of pore sizes as well as these sizes of interconnections between pores are very favorable for conduction of the cells, for bone regrowth and for tissue invasion, as was demonstrated by Karageorgiou et al., "Porosity of 3D biomaterial scaffolds and osteogenesis". *Biomaterials* 2005, 26, (27), 5474-5491.

However, in the case of this article, these pore shapes had been obtained on an implant made entirely of bioactive ceramic, i.e. of a calcium phosphate (hydroxyapatite).

Now, such ceramics have the drawback that they do not have the required flexibility for a bone implant. Their method of manufacture cannot be applied to a material comprising an organic part, like that of the invention, as it involves a step of sintering at temperatures of the order of 800° C., at which the organic part disintegrates.

Such size distributions are never achieved in implant materials comprising an organic part and an inorganic part derived from the methods of the prior art, for which the pores generally have sizes well below 200 µm with interconnections of far smaller sizes.

There are plenty of implant materials derived from the methods of foaming, but these then have very wide, uncontrolled size distributions of pores and interconnections, with a pore size that may even reach a millimeter, which is unfavorable for the mechanical behavior of the implant.

WO 2013/023064 describes a method for obtaining a matrix whose size allows infiltration of cells and internal bone growth. This matrix may be a fibrous matrix, which therefore does not have spherical pores as defined in the present invention, or else a matrix obtained by solvent molding. However, example 1B in this document, which describes obtaining a matrix by solvent molding, could not be reproduced owing to the excessive amount of porogenic agent (90% V/V of NaCl particles) used, which does not allow a homogeneous mixture to be obtained with the bioactive glass and the biodegradable polymer.

As will be seen later, thanks to the method for manufacturing a hybrid implant according to the invention, it is possible to control the dispersion of the set of sizes of pores and of interconnections of the matrix, which was not possible in the methods of the prior art, where the porosity generated is distributed randomly in their respective ranges.

The matrix 1 consists of an organic phase and an inorganic phase.

The inorganic phase is a bioactive glass M.

Bioactive ceramics and bioactive glasses are familiar to a person skilled in the art and are described in particular in L. L. Hench et al., J. Biomed. Mater. Res. 1971, 2, 117-141; L. L. Hench et al., J. Biomed. Mater. Res. 1973, 7, 25-42 for bioactive ceramics and in M. Vallet-Regi et al., Eur. J. Inorg. Chem. 2003, 1029-1042 and WO 02/04606, WO 00/76486 and WO 2009/027594, in particular. In the invention, only a bioactive glass is used.

The organic part of the implant material of the invention is a biodegradable polymer P soluble in at least one solvent S1 and insoluble in at least one solvent S. These solvents may be water, an aqueous medium or an organic solvent.

Preferably, the biodegradable polymer P is selected from:

bioabsorbable polysaccharides, preferably selected from dextran, hyaluronic acid, agar, chitosan, alginic acid, sodium or potassium alginate, galactomannan, carrageenan, pectin, bioabsorbable polyesters, preferably polyvinyl alcohol or poly(lactic acid), biodegradable synthetic polymers, preferably a polyethylene glycol, or poly(caprolactone), and proteins, preferably gelatin or collagen.

In the implant materials, the matrix 1 may consist of the bioactive glass M and the biodegradable polymer P, which form a composite material, i.e. the two phases bioactive glass M and biodegradable polymer P coexist in the architecture of the matrix. This material does not form part of the present invention.

In fact, the matrix 1 of the implant material of the invention consists of the bioactive glass M and of the biodegradable polymer P that form a hybrid material, i.e. form a single phase.

The hybrid material used in the invention is obtained by a method, which is also an object of the invention, that comprises the formation of a sol containing all the alkoxide precursors of the bioactive glass, addition of the biodegradable polymer P to this sol and gelation of the solution thus obtained by a succession of polymerization reactions (sol-gel polymerization of the inorganic phase) (condensation of the alkoxides).

A hybrid mixture is then obtained, intimately associating the mineral phase and the organic phase.

The hybrid material therefore differs from the composite material by intimate integration between the two phases, organic and inorganic, these two phases being indiscernible (except at the molecular scale) in the case of a hybrid mixture.

However, the matrix 1 may also be formed from the biodegradable polymer P alone, a polymer that is covered with bioactive glass M, for example by impregnation of the matrix 1 in biodegradable polymer P in a suspension of the bioactive glass M or by immersing the matrix 1 formed only of the biodegradable polymer P in a sol containing all the precursors of the bioactive glass M.

In both cases, the matrix 1 will then be dried to allow deposition of the particles of the bioactive glass M or gelation of the sol, as appropriate. This embodiment is not an object of the invention either.

The implant material of the invention is obtained by a method employing a porogenic agent A that consists of microspheres of a polymer soluble in at least one solvent S, in which the biodegradable polymer P is not soluble.

Thus, the method of the invention consists of stacking microspheres of porogenic agent A of a polymer material, different from the biodegradable polymer P, in a mold having the shape and size corresponding to the geometry of the bone defect to be filled or of the defect where bone regeneration is desired.

These microspheres of porogenic agent A make it possible to obtain, finally, pores whose size and distribution will correspond as a negative to the stack of microspheres of porogenic agent A initially produced.

Moreover, at least 70% by number of pores formed will have the shape of perfect spheres, i.e. will have either an equal diameter at all points, or the shape of spheres whose ratio of the smallest diameter to the largest diameter is 0.9±0.1, as a maximum, or for the largest pores, will have the shape of a polyhedron inscribed in a sphere having the same diameter at all points, the differences between the diameters at different points of the polyhedron inscribed in this sphere being at most approximately 15% of the diameter of the sphere in which they are inscribed.

In fact, the material intended to constitute the matrix 1 will then be infiltrated in the stack of beads of microspheres of porogenic agents A, then solidified so that it can be removed from the mold without changing the shape and size of the stack of the desired implant. The porogenic agent A will then be removed, allowing the implant material of the invention to be obtained.

As can be seen, this method does not use any high-temperature thermal treatment for sintering the bioactive glass M, the only temperature required being the temperature of evaporation of the solvent S used.

The same applies to the case when the matrix 1 consists only of the biodegradable polymer P, which is then covered with the bioactive glass M.

As will become clear, the invention is based on a judicious combination of the choice of three materials: the material constituting the biodegradable polymer P, the material constituting the porogenic agent A and the solvent S of the porogenic agent A, which must not dissolve the biodegradable polymer P.

The material of the biodegradable polymer P that forms part of the implant material must be a biocompatible polymer.

For its part, the material of the porogenic agent A must be a material, for example a polymer, for which the solvent S is a nonsolvent of the biodegradable polymer P.

It will then be understood that the choice of one of the three elements of the trio "biodegradable polymer P-porogenic agent A-solvent S of the porogene" cannot be made independently of the choice of the others.

The biodegradable polymers P must be soluble in at least one solvent S1, which may be water or aqueous solutions or else an organic solvent, and insoluble in at least one solvent S different from the solvent S1. This solvent S may also be water, an aqueous medium or an organic solvent.

The preferred biodegradable polymers P that can be used include:

bioabsorbable polysaccharides, preferably selected from dextran, hyaluronic acid, agar, chitosan, alginic acid, sodium or potassium alginate, galactomannan, carrageenan, pectin;

bioabsorbable polyesters, preferably polyvinyl alcohol; or polylactic acid, biodegradable synthetic polymers, preferably a polyethylene glycol, or polycaprolactone, and proteins, preferably gelatin or collagen.

The material constituting the porogenic agent A must be soluble in the at least one solvent S in which the biodegradable polymer P is insoluble.

Examples of such materials are the biodegradable polymers that are insoluble in an aqueous medium and soluble in the at least one solvent S, preferably selected from $C_1$ to $C_4$ polyalkyl methacrylates, preferably polymethyl methacrylate or polybutyl methacrylate, polyurethane, polyglycolic acid, the various forms of polylactic acids, the copolymers of lactic-coglycolic acids, polycaprolactone, polypropylene fumarate, paraffin and naphthalene, or acrylonitrile butadiene styrene (ABS).

In all cases, the solvent S of the material of the porogenic agent A will not have to be a solvent for the material selected to serve as biodegradable polymer P and, of course, the material of the porogenic agent A will have to be different from the biodegradable polymer P.

The solvents S are in particular acetone, ethanol, chloroform, dichloromethane, hexane, cyclohexane, benzene, diethyl ether, hexafluoroisopropanol.

In the invention, preferably, the biodegradable polymer P will be gelatin, the microspheres of porogenic agent A will be of polymethyl methacrylate and the solvent S will be acetone.

In the method for manufacturing the hybrid implant material of the invention, the microspheres may be placed in the mold before introduction of the mixture of the alkoxide precursors of the bioactive glass M and of the biodegradable polymer P.

However, it is also possible to put the mixture of the alkoxide precursors of the bioactive glass M and of the biodegradable polymer P in the mold first, and then pour in the microspheres of porogenic agent A.

It is also possible to prepare a mixture of the alkoxide precursors of the bioactive glass M, the biodegradable polymer P and the microspheres of porogenic agent A, and put this mixture in the mold.

To obtain a material in which at least 70% by number of pores have at least one interconnection with another pore, the amount of porogenic agent A added to the biodegradable polymer P-bioactive glass M mixture must represent at least 60 vol % of the total volume of the biodegradable polymer P-bioactive glass M-porogenic agent A mixture introduced into the mold.

The size of the interconnections is related to the size of the point of contact between spheres of porogenic agent A in the stack of spheres produced. The size of the interconnections generated, at constant pore diameter, can be increased by adding a step consisting of partial fusion of the porogenic spheres in the stack initially produced, so as to increase the size of their point of contact.

The microspheres of porogenic agent A must form a compact stack, when placed in the mold with, in the invention, the sol of the alkoxide precursors of the bioactive glass M and the biodegradable polymer P.

For this, the volume of porogenic agent A, relative to the total volume of the biodegradable polymer P-precursors of bioactive glass M-porogenic agent A mixture, must be at least 60%, preferably at least 70%.

As for the biopolymer P/bioactive glass M weight ratio, it may be between 10/90 and 90/10. Preferably, for reasons of the mechanical behavior of the material obtained, it will be between 20/80 and 80/20, the best mechanical behavior (easy manipulation without distortion or loss of material) being obtained with a 70/30 ratio. This fusion may be done by infiltration of the solvent S of the porogenic agent A on the stack of the porogenic agent A, or else by heating the stack of microspheres of porogenic agent A produced, or else both at the same time, so as to produce superficial dissolution of the spheres and allow their partial fusion.

FIGS. 6 to 8 show the effect of increasing the size of these interconnections by infiltration of an acetone-ethanol mixture at 30 vol % of acetone, relative to the total volume of the mixture, on a stack of microspheres of porogenic agent A which are of poly(methyl methacrylate), after 15 min, 30 min and 1 hour of infiltration.

This infiltration takes place directly on the stack of microspheres of porogenic agent A, before introduction of the bioactive glass M and/or of the biodegradable polymer P.

Figure 1:
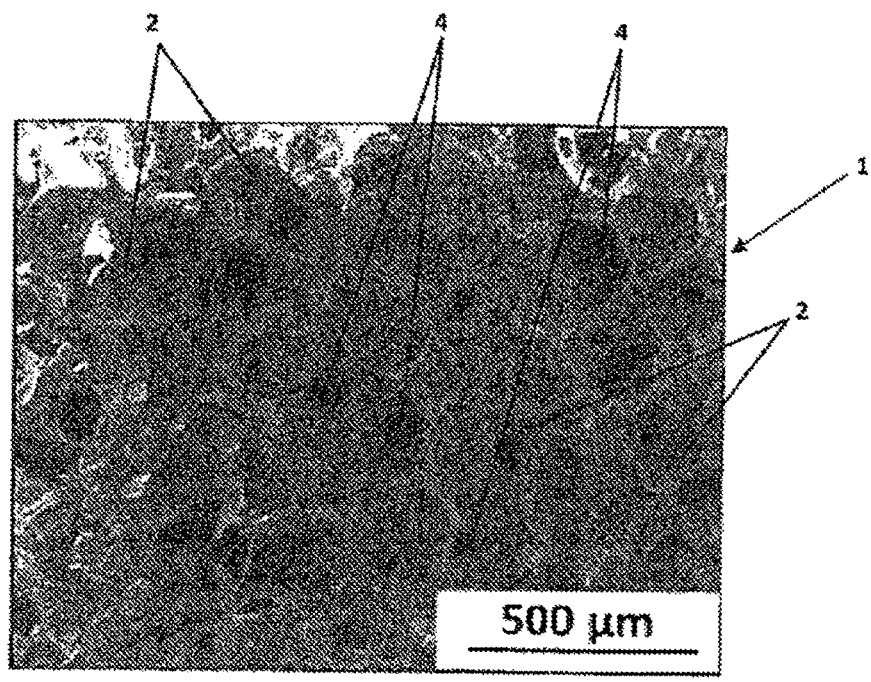
Figure 2:
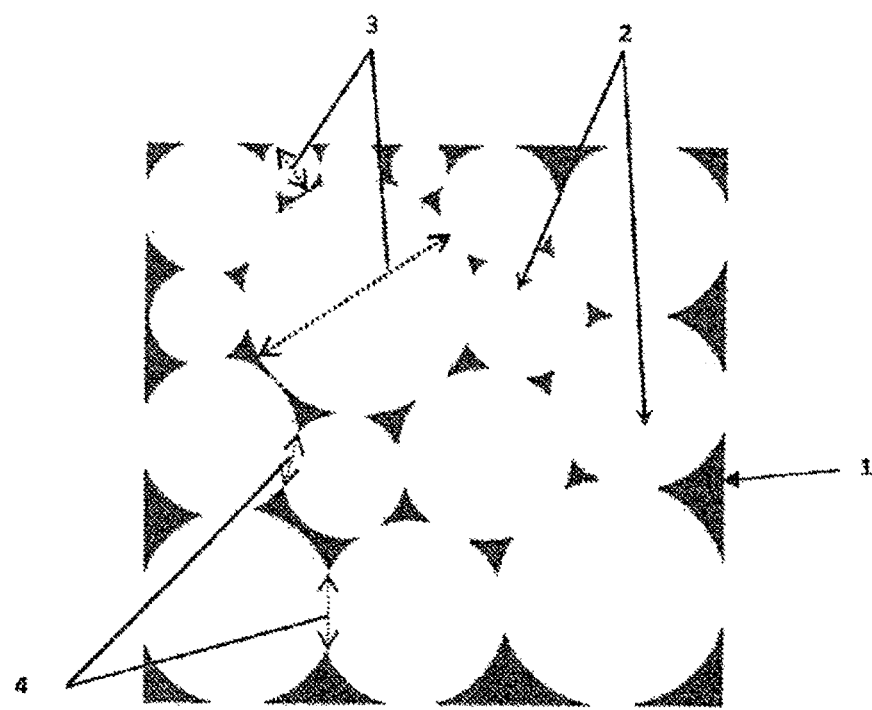
Figure 3:
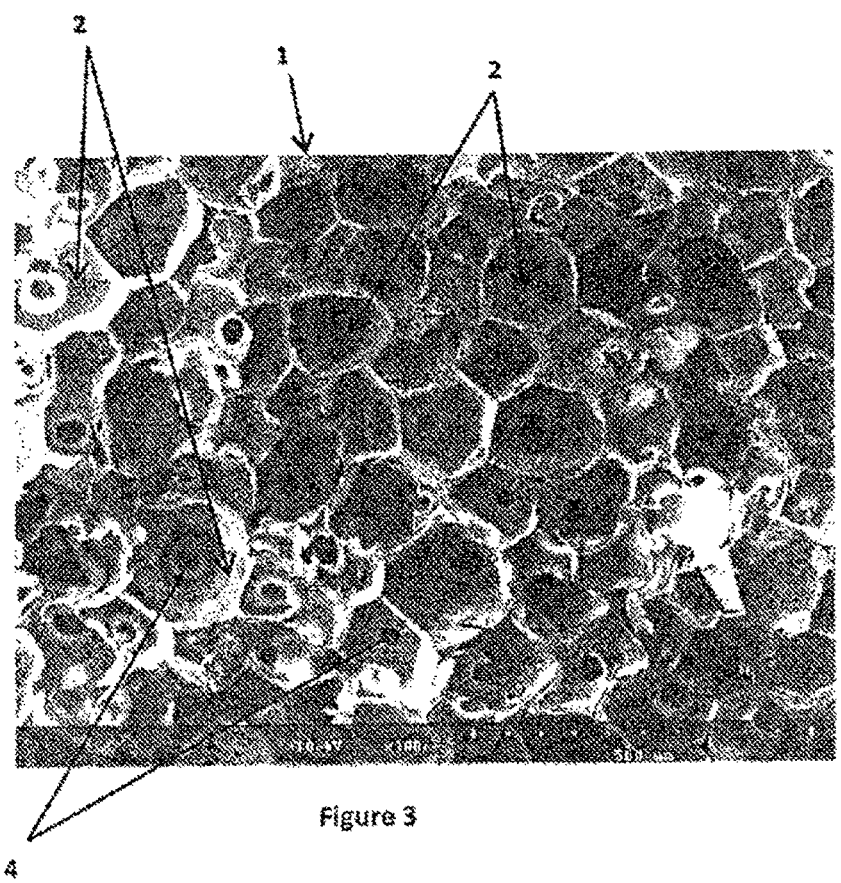
Figure 4:
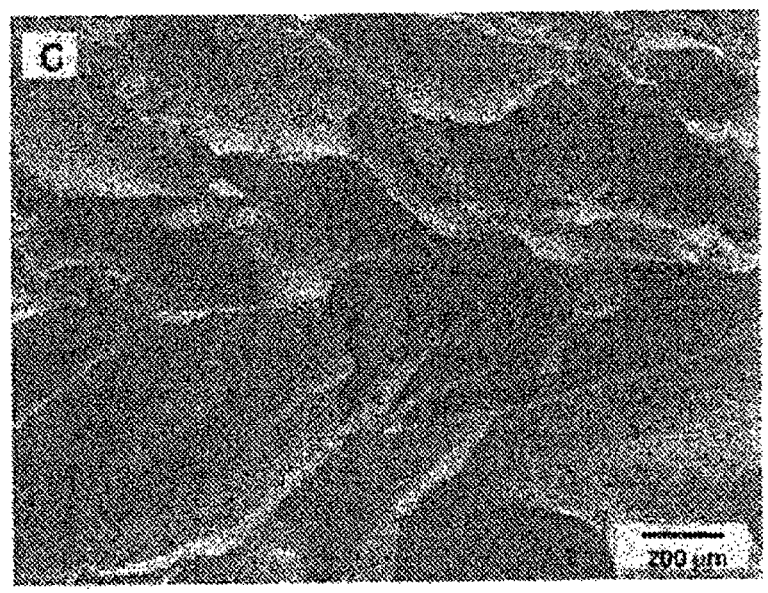
Figure 5:
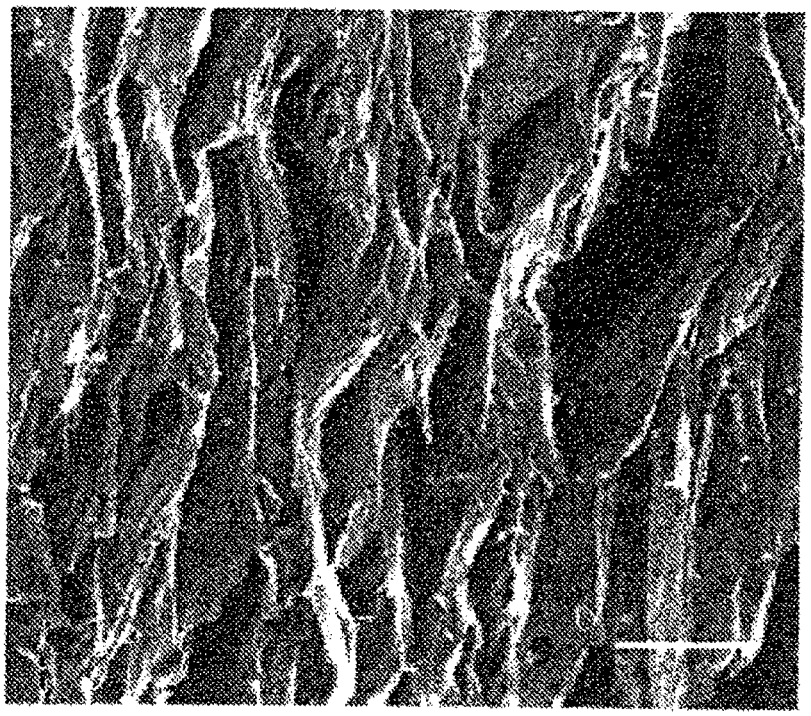
Figure 6:
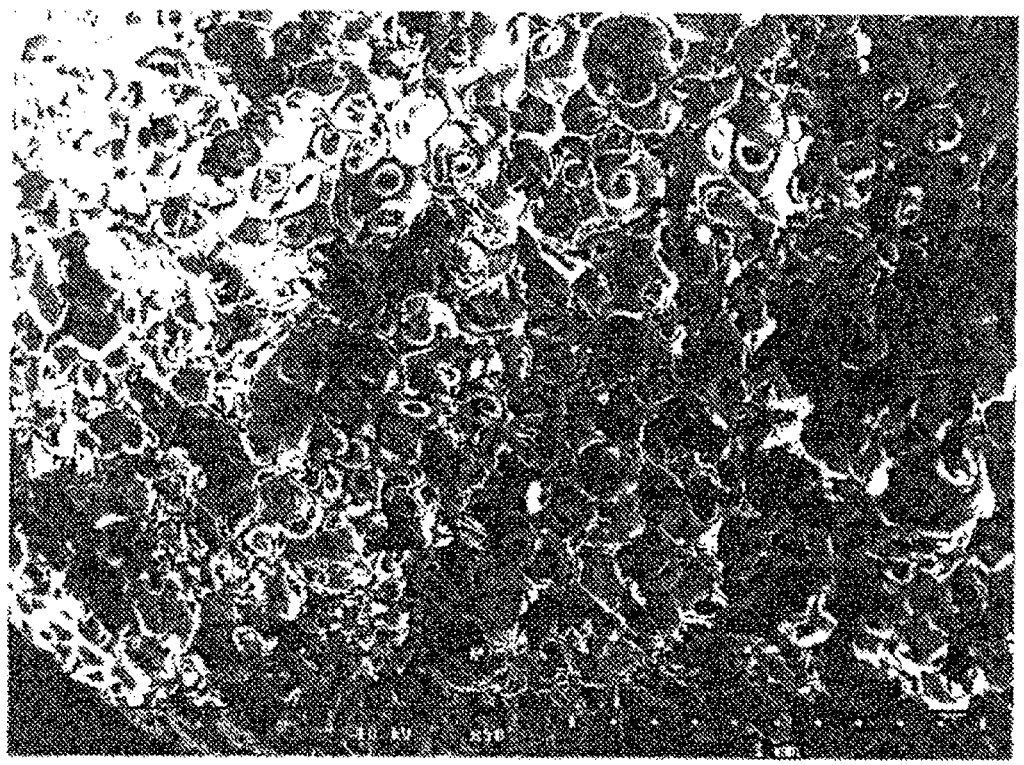
Figure 7:
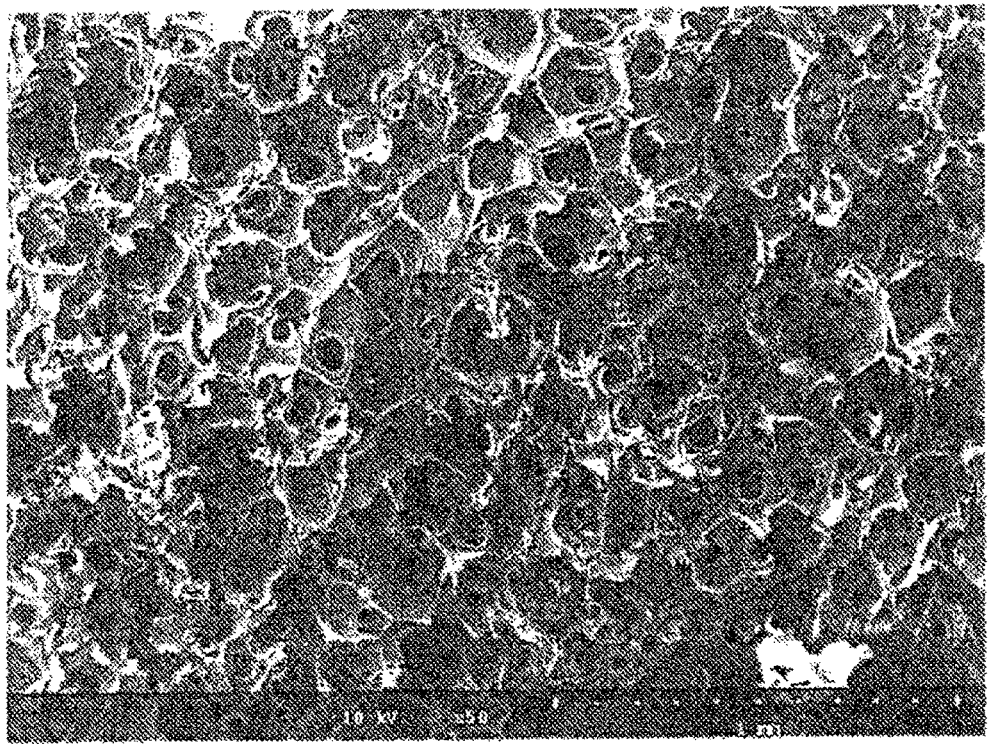
Figure 8:
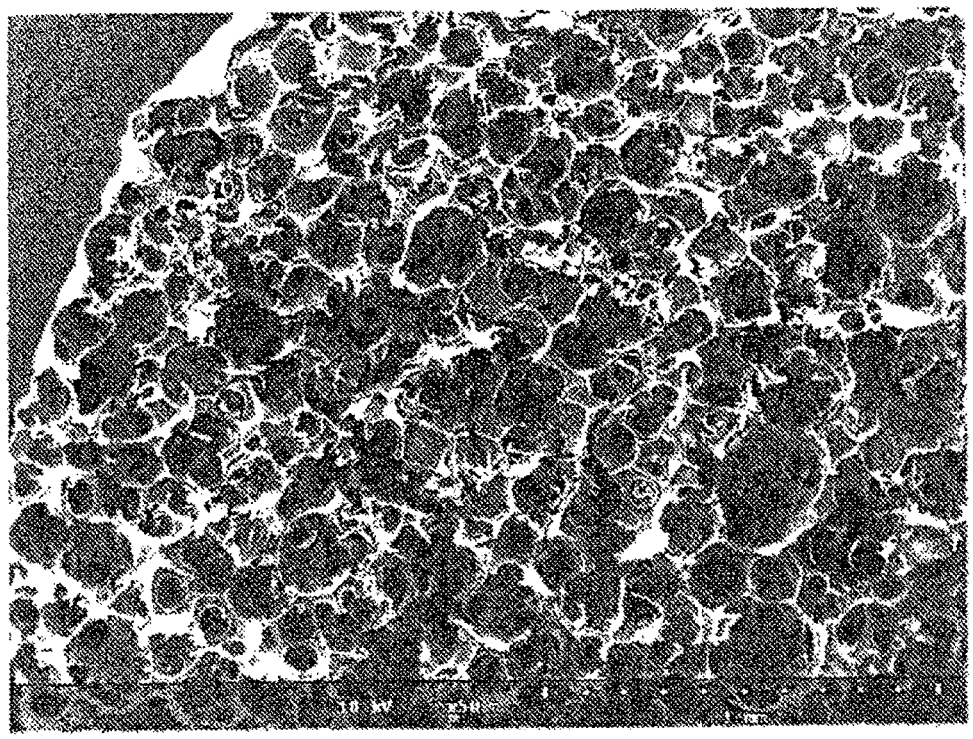
Figure 9:
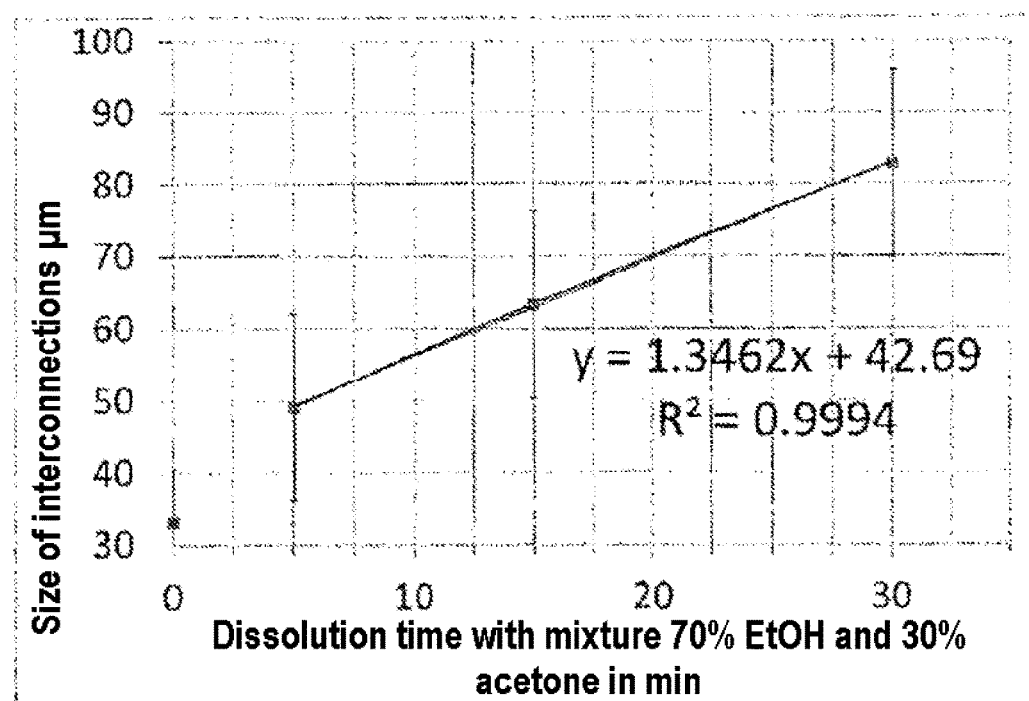
FIG. 9 shows the effect of this increase in the form of a curve.
Figure 10:
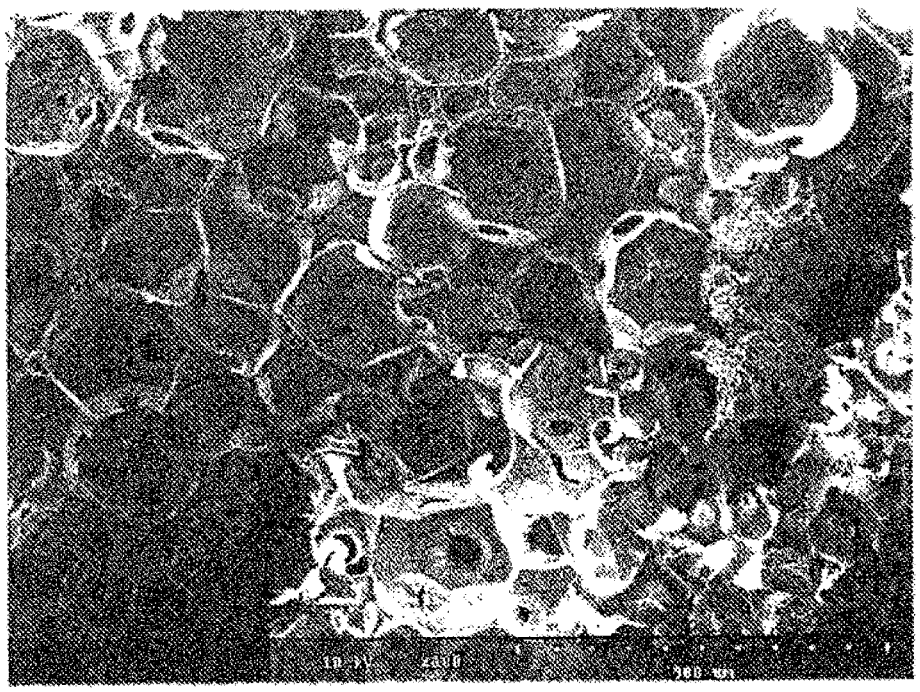
FIGS. 10 to 12 show the effect of increasing the size of these interconnections by heating the stack of microspheres of porogenic agent A at 125° C., before introduction of the bioactive glass M and/or of the biodegradable polymer P, for 15 min, 1 hour and 2 hours.
Figure 11:
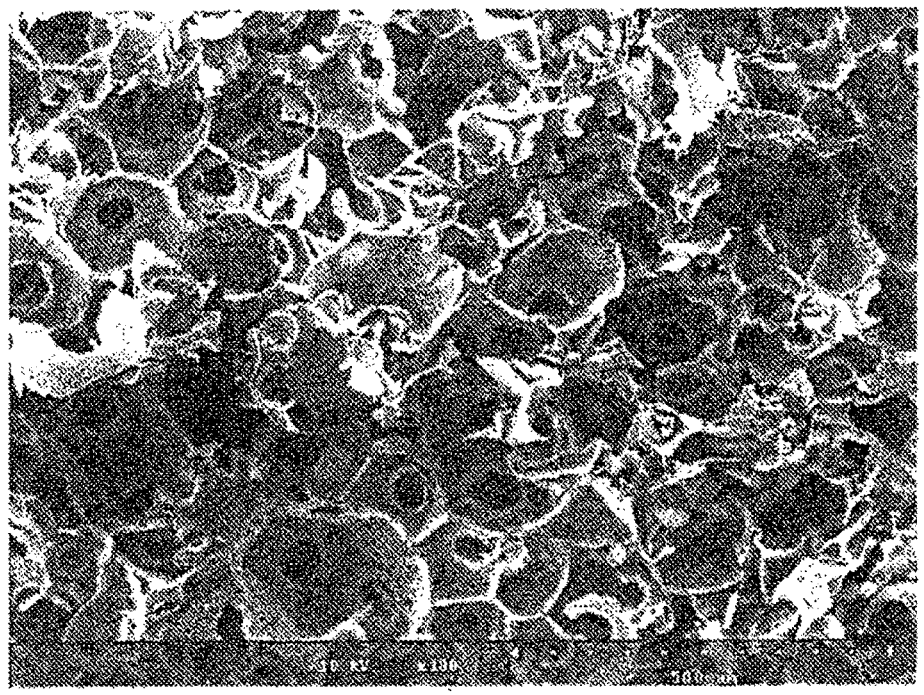
Figure 12:
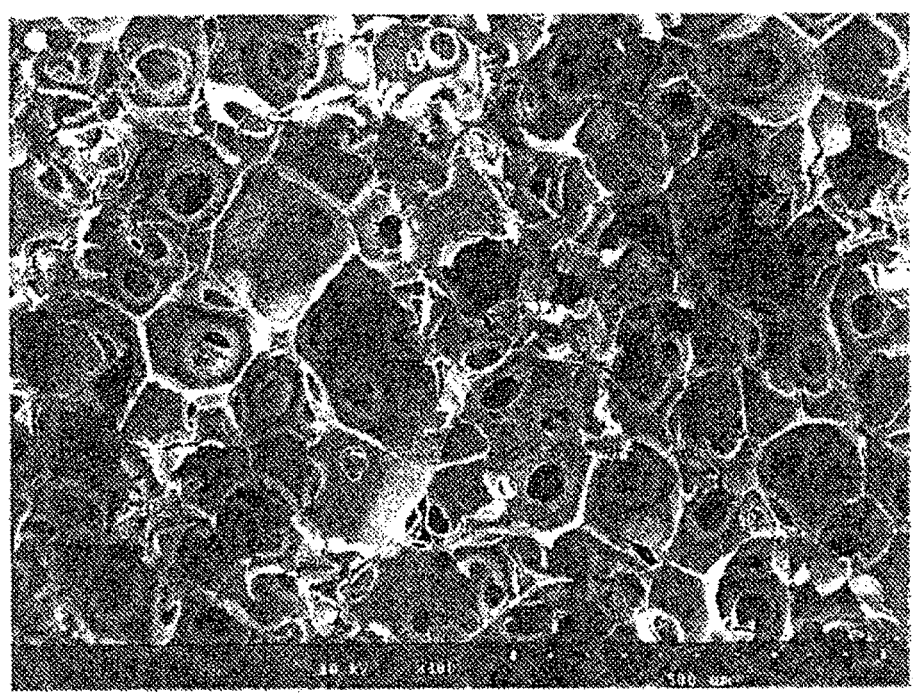
Figure 13:
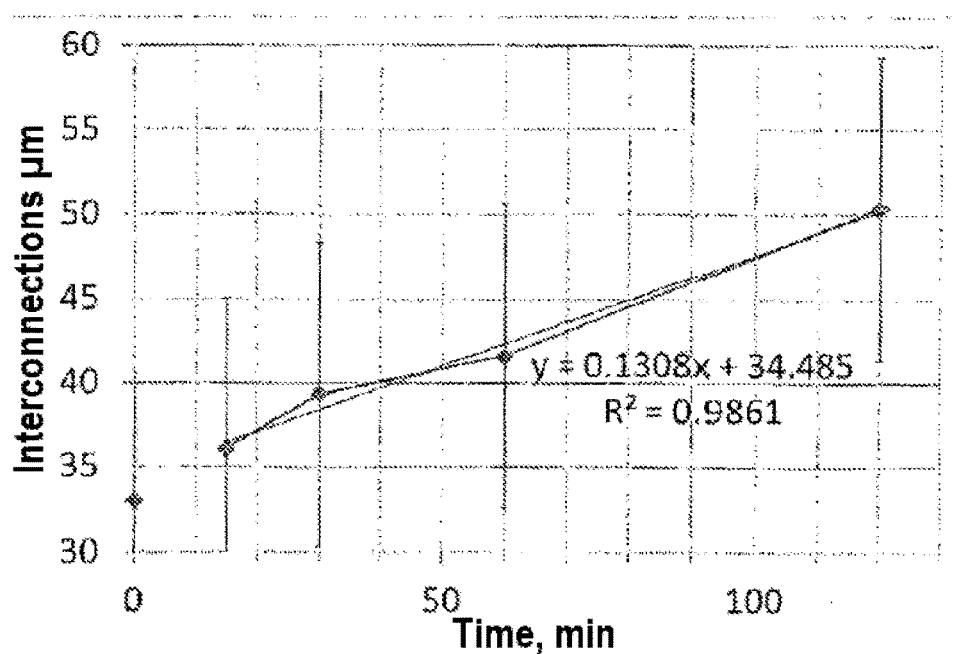
FIG. 13 shows the effect of this increase in the form of a curve.

For better understanding of the invention, several embodiment examples will now be described, purely for illustration, and nonlimiting.

EXAMPLE 1

Manufacture of an implant made of a composite material comprising, as biodegradable polymer P, gelatin and a bioactive glass M consisting of 75% of $SiO_2$ and 25% of CaO, by weight, relative to the total weight of the glass, as bioactive glass M (not part of the invention).

Gelatin was selected as the material for the biodegradable polymer P because it is a natural, biocompatible biopolymer that is inexpensive and readily available. Moreover, gelatin is derived from collagen, which is present naturally in bones. Furthermore, it is already used in the context of clinical applications, dressings, adhesives and encapsulation of pharmaceuticals.

A bioactive glass was selected on account of its great capacity for inducing mineralization, the possibility of shaping its textural and morphological properties (porosity, size and therefore specific surface area) at the nanometric scale, the wide range of bioactive compositions that it is possible to formulate, for example by adding anti-inflammatory, or osteoinducing elements, and finally it is the combination of their properties of bioactivity and bioabsorbability that makes them the most promising biomaterials for bone regeneration, notably relative to calcium phosphates (bioactive ceramics), which are generally either less bioactive, or less absorbable.

The microspheres are microspheres of polymethyl methacrylate. This material was selected as it can easily be dissolved by numerous solvents.

Moreover, if residues of polymethyl methacrylate not removed were to remain in the implant material, the good biocompatibility of this polymer with human tissues is a good guarantee that the implant will not present any risk of cytotoxicity.

The porogenic agent was in the form of spherical particles, namely beads of polymethyl methacrylate with a diameter between 200 and 400 µm. It represented 60 vol % of the total volume of the mixture (porogenic agent A-biodegradable polymer P-bioactive glass M) introduced into the mold.

Their diameters may be selected between several tens and several hundreds of microns, depending on the applications. The porosity of the implant material of the invention that will finally be obtained can be controlled for these two points; firstly the diameter of the pores that will be obtained depends directly on the diameter of the initial porogenic particles. It is therefore sufficient to adjust the granulometry of the initial microspheres of polymethyl methacrylate to obtain the desired porosity very simply. Secondly the size of the interconnections between pores depends directly on the size of the contact zone between the polymer beads in the initial stack. The size of this contact zone can be modified by fusing the initial polymer particles together, by means of a solvent S, or by a preliminary thermal treatment. This procedure has already been described by Descamps et al., "Manufacture of macroporous beta-tricalcium phosphate bioceramics". *Journal of the European Ceramic Society* 2008, 28, (1), 149-157 and "Synthesis of macroporous beta-tricalcium phosphate with controlled porous architectural". *Ceramics International* 2008, 34, (5), 1131-1137.

In this example, the biodegradable polymer and the bioactive glass were used for obtaining a composite matrix.

Thus, for this example, the first step consisted of placing particles of porogenic agents consisting of microspheres of polymethyl methacrylate in a mold with the size and shape required for the implant.

In a second step, the powder of bioactive glass was introduced.

The granulometry of the powder of bioactive glass plays an important role in obtaining a homogeneous composite matrix. Preferably, the granulometry of the powder of bioactive glass must be well below 50 Ideally, the powder particle size must be of the order of a micrometer, or even of the order of a nanometer to a few hundred nanometers. Such fineness can be obtained with a planetary ball mill, for example.

In a third step, gelatin, previously dissolved in lukewarm water, was put in the mold. The composite mixture is then homogenized.

In a fourth step, the mixture obtained in the third step is gelled for several hours, in the mold, partial dehydration of the gelatin ensuring setting of the mixture.

This operation is carried out at a temperature between 0° C. and 60° C. inclusive, so as not to degrade the matrix.

In a fifth step, the microspheres of polymethyl methacrylate porogenic agent are removed by washing with acetone.

Acetone offers several advantages: firstly, the polymethyl methacrylate beads are easily dissolved in acetone, whereas gelatin is insoluble in acetone.

In addition, acetone makes it possible to continue dehydration of the gelatin, if required.

Finally, it is a solvent in very common use, relatively economical, readily available, without any serious risks of toxicity.

After several washing steps, the initial imprint of the microspheres of polymethyl methacrylate is removed completely and the final material is obtained, in the form of a bio-composite macroporous block of bioactive glass/gelatin.

The biodegradability of this implant material in a living environment and its mechanical behavior may, moreover, easily be adjusted by crosslinking the gelatin in a final step of immersion in a solution of a crosslinking agent, for example genipin, carbodiimide, glutaraldehyde, formaldehyde.

However, this step is optional.

The structures obtained can be washed without any damage in baths of ethanol, in order to remove any undesirable residues, such as chlorides, acetone, etc.

In this example, an implant material was obtained comprising 60 wt % of bioactive glass and 40 wt % of gelatin, relative to the total weight of the implant and having 70% by number of pores having at least one interconnection with another pore.

EXAMPLE 2

Manufacture of an implant material according to the invention with a matrix of hybrid material.

This started with the step of stacking the microspheres of porogenic agent polymethyl methacrylate in a mold having the geometry required for the implant. The volume of the microspheres of porogenic agent A represented 70% of the total volume of the mixture of porogenic agent A-biodegradable polymer P-precursors of the bioactive glass M. The material of the porogenic agent A was poly(methyl methacrylate). The spheres had a diameter between 200 and 400 μm.

In a second step, the hybrid mixture was poured into the mold containing the stack of beads.

Centrifugation or infiltration under pressure or infiltration under vacuum may be used to ensure that the hybrid mixture fills the interstices between the microspheres of poly(methyl methacrylate).

The hybrid material was obtained by a sol-gel technique.

In this technique, a sol containing all the alkoxide precursors of the bioactive glass is caused to undergo gelation by a succession of polymerization reactions.

The alkoxide precursors were in amounts such that the composition of the bioactive glass was 75% $SiO_2$ and 25% CaO, by weight, relative to the total weight of the bioactive glass finally obtained.

In the present example, gelatin (the biodegradable polymer P) was added before gelation of the sol, so as to obtain a hybrid mixture.

For making the hybrid material, a major difficulty is that thermal treatments at high and moderate temperature, i.e. above 150° C., are to be avoided.

Now, in the methods described in the prior art and notably in Lin, S. et al., "Nanostructure evolution and calcium distribution in sol-gel derived bioactive glass". *Journal of Materials Chemistry* 2009, 19, (9), 1276-1282, these thermal treatments are indispensable for obtaining a homogeneous vitreous network, notably for incorporating calcium in the silicate network.

The use of an alkoxide precursor for calcium makes it possible to incorporate calcium in the inorganic phase without thermal treatment.

However, the very great reactivity of the calcium alkoxides with respect to reactions of hydrolysis/condensation in the presence of water means that the sol obtained is very unstable, sol-gel polymerization taking place extremely rapidly, which to date has made it impossible to manipulate it for making a porous implant, and moreover has not allowed good incorporation of calcium in the silicate network. Thus, the inventors discovered that by limiting addition of water to the sol to the maximum extent and by using an alkoxide precursor different from that used in the literature (Ramila A. et al., "Synthesis routes for bioactive sol-gel glasses: alkoxides versus nitrates". *Chemistry of Materials* 2002, 14, (12), 542-548) (namely calcium methoxyethoxide), it is possible to increase the stability of the sol considerably. The reactions of hydrolysis/condensation are then slow enough to allow homogeneous incorporation of calcium in the silicate network, while remaining fast enough to allow polymerization of the inorganic phase. In the example, the alkoxide precursors of silicon and calcium are mixed together in a lightly acidified alcoholic solution. Preferably, the alkoxide precursors are tetraethoxysilane and calcium ethoxide. Then the gelatin, previously dissolved, is added to this mixture to obtain a hybrid sol. Water is only supplied via the acid and the gelatin solution: this is sufficient to allow the reactions of hydrolysis/condensation while limiting them strongly so as to have a sol that is stable and can be manipulated for between some minutes and some hours depending on the proportions of the reactants.

The implant material of the invention is then obtained by applying the fourth and fifth steps as carried in example 1.

Whether during preparation of the composite mixture or of the hybrid mixture, it may be advantageous to add a coupling agent, such as an organo-alkoxysilane, to the mixture.

In fact, two classes of organic-inorganic hybrid implants can be produced, depending on the nature of the interface between the organic component (biocompatible polymer) and the inorganic component (bioactive glass). Class I corresponds to hybrid systems in which the two components interact by weak bonds (hydrogen bonds, van der Waals bonds, or electrostatic bonds). In class II, in contrast, the organic-inorganic components are bound strongly by covalent bonds or ionic-covalent bonds. This can be obtained by means of a coupling agent.

For example, the coupling agent may simply be added to the aqueous solution of the biodegradable polymer P, in this case gelatin. The role of the coupling agent is to functionalize the gelatin, to allow the establishment of covalent bonds with the inorganic phase (silicate network of the bioactive glass). In the case of a composite mixture, coupling makes it possible to obtain particles of bioactive glass bound at the surface to the gelatin. In the case of a hybrid mixture, a true organo-mineral copolymer (hybrid of class II) is obtained. The advantage is to be able to tailor the degradability of the composite or hybrid implant as well as its mechanical behavior, simply by acting on the degree of affinity between organic and inorganic phases.

An example of coupling agent used successfully in the invention is GPTMS (3-glycidoxypropyltrimethoxysilane), which is soluble in an aqueous solution of gelatin.

An implant material was obtained consisting of 70 wt % of gelatin and 30 wt % of bioactive glass.

EXAMPLE 3

Manufacture of an implant material with a matrix of biodegradable polymer p covered with bioactive glass (not part of the invention).

The procedure as in example 2 was followed, except that in the second step, only gelatin was added, and after the fifth step, removal of the microspheres of polymethyl methacrylate by washing, the biodegradable polymer P, in this case gelatin, was crosslinked in a solution of glutaraldehyde.

The amount of porogenic agent A was 70 vol % relative to the total volume of porogenic agent A-biodegradable polymer P introduced into the mold.

Then the matrix of biodegradable polymer P is immersed in a suspension of the bioactive glass M or else immersed in a sol containing all the alkoxide precursors of the bioactive glass M.

In both cases, the matrix 1 is then dried to allow deposition of the particles of bioactive glass M or gelation of the sol, as appropriate.

EXAMPLE 4

Manufacture of a hybrid material by the method of the invention.
Products Used:
Tetraethyl orthosilicate TEOS
Calcium ethoxide Ca(OEt)$_2$
3-Glycidoxypropyltrimethoxysilane GPTMS
2M HCl and 10 mM HCl
Absolute ethanol
Gelatin type B
Acetone
Protocol:
1. Fill a polyethylene tube with height of 32 mm and diameter of 9 mm with PMMA beads to a height of about 10 mm.
2. Mix 7.80 g of TEOS and 6.39 g of ethanol in a bottle.
3. Stir for 15 min using a magnetic stirrer.
4. Add 1.35 mL of 2M HCl to the Ethanol+TEOS mixture.
5. Stir for 30 min.
6. Weigh 6.39 g of ethanol in another bottle.
7. Add 1.74 g of calcium ethoxide.
8. Stir for 15 min.
9. Add the sol containing TEOS to the solution of calcium ethoxide.
10. Stir for at least 1 hour.
11. Dissolve 1.26 g of type B gelatin and 0.63 g of GPTMS in 8.74 g of 10 mM HCl in a water bath at 60° C.
12. Take 3 g of bioglass sol and add 7 g of GPTMS grafted gelatin sol to a bottle.
13. Stir for a few minutes, with a magnetic stirrer.
14. Add the hybrid sol to the PMMA beads.
15. Centrifuge for 1 min.
16. Leave to gel at a temperature between 0° C. and 60° C., for at least 24 hours.
17. Remove the hybrid block obtained from the mold.
18. Dissolve the PMMA beads in a bottle filled with acetone, renewing the acetone after 24 hours. This operation is to be repeated twice.
19. Recover the porous block obtained and put it in a stove to dry at 60° C. for 24 hours.

An implant material was obtained consisting of a hybrid material of class II consisting of 70 wt % of biodegradable polymer P and 30 wt % of bioactive glass M.

EXAMPLE 5

Preparation of composite porous implants with 60% of bioglass (75% SiO$_2$-25% CaO) and 40% of gelatin (wt %) (not part of the invention).

1) Synthesis of the Glass Powder by the Sol-Gel Route 13.48 mL of water and 13.48 mL of ethanol are mixed with 2.25 mL of 2N HCl and then 13.94 mL of TEOS is added. After stirring for 30 minutes, 5.2637 g of Ca(NO$_3$)$_2$.4H$_2$O is added. The sol is stirred for 1 hour, put in a stove at 60° C. in Teflon containers for 24 h and then put in the air at 125° C. for 24 h. The powder thus obtained is then calcined for 24 hours at 700° C. (heating from 25 to 700° C. carried out in 2 hours).

The powder is then ground for 30 minutes and then sieved, only keeping the fraction below 50 μm.

2) Preparation of the Composite

Porcine gelatin powder (type A) is added to distilled water heated to 35° C. in a ratio of 0.1 g/mL of water; the mixture is stirred for 10 minutes. In parallel, an amount of 0.025 g of glass powder is mixed with 0.2 g of PMMA beads with diameters between 100 and 300 μm and representing 60 vol % of the total volume of the mixture introduced into the mold. 0.15 mL of gelatin solution in water is then added, and the mixture obtained is poured into a tube, in which it is compacted.

After drying for 1 day in the ambient air, the glass cylinder+beads+gelatin is taken out of the mold and immersed in acetone for 6 hours with stirring; the acetone is then renewed and dissolution is allowed to continue for 24 hours, still with stirring. The porous glass-gelatin composite block obtained is then rinsed with acetone and dried in the ambient air. It consists of 60 wt % of bioactive glass and 40 wt % of biodegradable polymer.

EXAMPLE 6

In vitro evaluation of the implants obtained in examples 1 to 5.

The bioactivity of the implant materials obtained in examples 1 to 3 was evaluated in vitro by immersing them in a physiological solution (SBF) having an ion composition identical to that of blood plasma (ISO-23317 test).

Then the great bioactivity that is typical of the bioactive glasses used in the implant materials was verified: these implant materials were found to be very prompt in inducing mineralization in contact with the physiological medium: after 1 h of interaction with the medium, some of the calcium ions derived from the vitreous matrix have migrated to the surface of the composite, where phosphate ions derived from the physiological medium have been incorporated to form a layer of calcium phosphate about ten microns thick, which coats the surface of the pores.

This constitutes the first step of the bioactivity process.

It was verified that subsequently this layer of calcium phosphate continues to grow, to form an apatite layer similar to bone mineral.

Crosslinking of the gelatin does not diminish the bioactivity of the implant, but makes it possible to increase its resistance to dissolution in the physiological medium.

It was also noted that the SBF medium is quickly (after 1 day) exhausted of phosphorus, and to a less extent of calcium, these elements being incorporated at the surface of the implants and therefore withdrawn from the medium to form a biomimetic layer of calcium phosphate.

Crosslinking of the gelatin does not in any way alter the chemical reactivity of the implants, but offers the advantage of making it possible to adjust their biodegradability in a living environment.

Thus, all the materials manufactured in examples 1 to 5 prove to be prompt at inducing formation of bone mineral in contact with physiological fluids.

However, it is noted there are differences between these materials.

Firstly, the materials in which gelatin has been crosslinked have a slower biodegradability, which is manifested by slower dissolution of silicon. The formation of calcium phosphates is also slower.

Next, it can be seen that formation of calcium phosphates on the surface of the material is slower with the composite material than with the material consisting of the biodegradable polymer P coated with the bioactive glass M and than with the hybrid material of the invention.

With the composites and biodegradable polymer coated with bioactive glass as expected, formation of calcium phosphates and in particular of apatite only occurs on the surface of the material.

In contrast, and surprisingly, with the hybrid material, formation of calcium phosphates takes place not only on the surface but also in the bulk, which represents a definite advantage, especially when the bone defect to be filled requires rapid integration.

COMPARATIVE EXAMPLE

Manufacture of an implant according to WO 2013/023064.

Porcine gelatin powder (type A) is added to distilled water heated to 35° C. in a ratio of 0.1 g/mL of water; the mixture is stirred for 10 minutes. An amount of 0.75 g of glass powder is mixed with 57.38 g of NaCl particles, then 4.5 mL of the gelatin solution is added, in such a way that the volume of porogene represents 90% of the total volume of the mixture, as stated in WO 2013/023064. The mixture obtained is poured into a tube. The mold and its mixture then undergo freezing, and then lyophilization under vacuum for 1 day. After lyophilization, the composite block is removed from the mold and immersed in distilled water in order to dissolve the porogene (NaCl).

Unfortunately, the amount of porogene (90% of the total volume) proved to be much too great relative to the amount of composite mixture: dissolution of the porogene led to immediate destruction of the composite structure, and no implant could be obtained by this production protocol.

EXAMPLE 7

Manufacture of an implant material with a matrix of hybrid material of class II, in which the biodegradable polymer P is poly(D,L-lactic acid).

The procedure as in example 2 was followed, except that the gelatin was replaced with a poly(D,L-lactic acid) (PDLLA) of class II.

The composition of the bioactive glass was 75% of $SiO_2$ and 25% of CaO, by weight, relative to the total weight of the glass, and the final implant material had the composition 30% bioactive glass-70% PDLLA, by weight, relative to the total weight of the implant material obtained.

The porogenic agent A was spherical particles of paraffin with a diameter between 400 and 600 μm.

The microspheres represented 70 vol % of the total volume of the mixture introduced into the mold.

Figure 15:
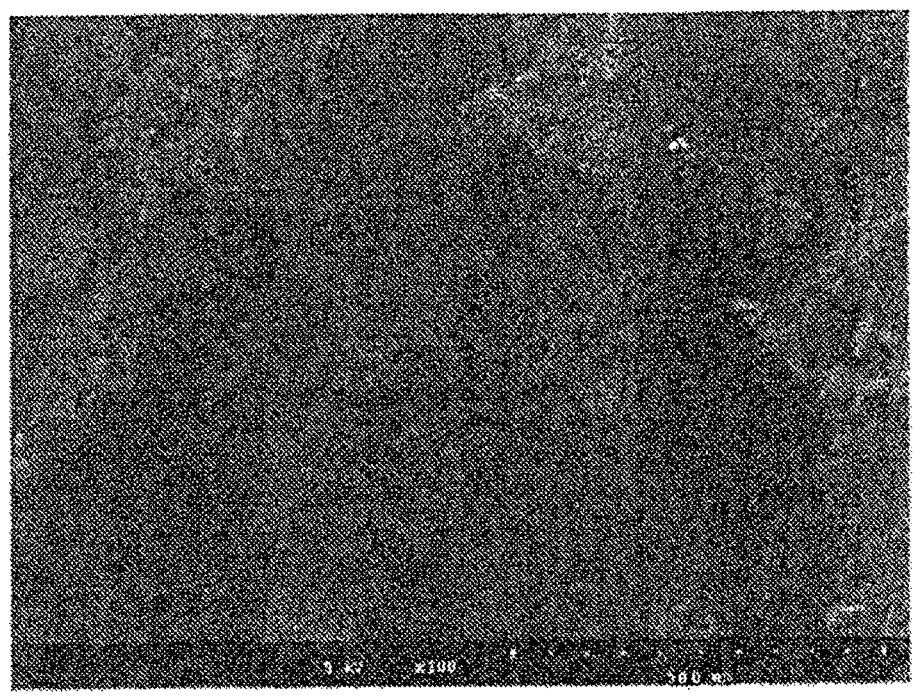

As can be seen in FIG. 15, the implant material obtained has more than 70% by number of interconnected spherical pores.

Solvent S1 was acetone.

Solvent S was cyclohexane.

EXAMPLE 8

Manufacture of an implant material according to the invention with a matrix of hybrid material of class II in which the biodegradable polymer P is chitosan.

The procedure as in example 2 was followed, except that gelatin was replaced with chitosan.

The bioactive glass used had the composition by weight 75% $SiO_2$-25% CaO and the implant material obtained had the composition 30% bioactive glass-70% chitosan, by weight, relative to the total weight of the implant material.

The porogenic agent A was spherical particles of poly (methyl methacrylate) (PMMA) with a diameter of 200 μm. It represented 70 vol % of the total volume of the mixture introduced into the mold.

Solvent S1 was an acidic aqueous solution (pH=2).

Solvent S was acetone.

Figure 16:
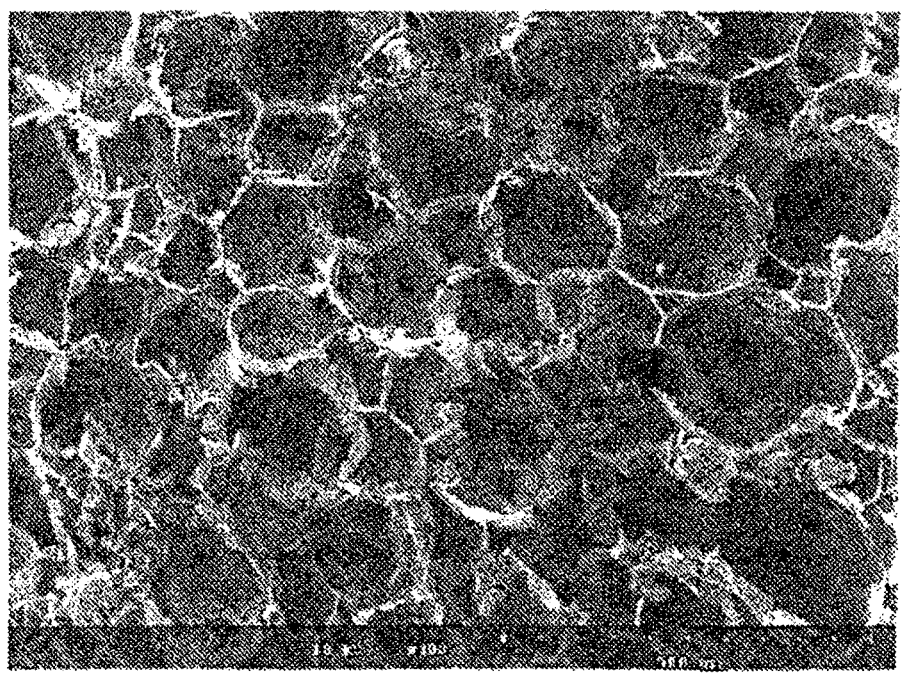

As can be seen in FIG. 16, this implant material has spherical pores, all of them having at least one interconnection with at least one other pore.

In this implant material, more than 90% by number of the pores are spherical.

EXAMPLE 9

Manufacture of an implant material according to the invention with a matrix of hybrid material of class II in which the biodegradable polymer P is polyethylene glycol with weight-average molecular weight equal to 35 000.

The procedure as in example 2 was followed, except that gelatin was replaced with polyethylene glycol with a weight-average molecular weight of 35 000.

The bioactive glass had the composition 75% $SiO_2$-25% CaO, by weight, relative to the total weight of the bioactive glass finally obtained and the implant material obtained had the composition 30% bioactive glass-70% PEG, relative to the total weight of the implant material.

The porogenic agent A was spherical particles of paraffin with a diameter between 200 and 400 μm. These particles represented 70 vol % of the total volume of the mixture introduced into the mold.

Solvent S1 was ethanol heated to 60° C.
Solvent S was cyclohexane.

Figure 17:
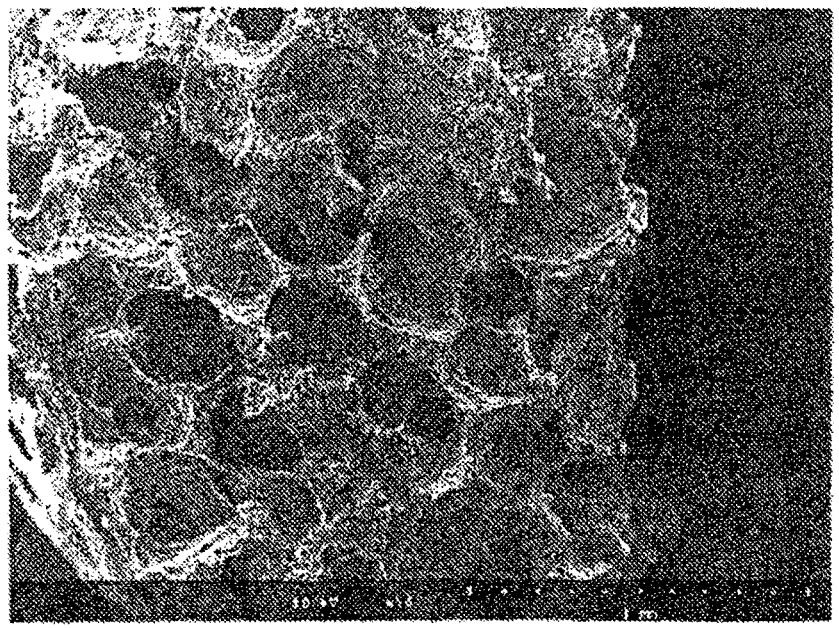

As can be seen in FIG. 17, an implant material is obtained having more than 90% by number of spherical pores having at least one interconnection with at least one other pore.

EXAMPLE 10

Manufacture of an implant material according to the invention with a matrix of hybrid material of class II in which the biodegradable polymer P is poly(vinyl alcohol) (PVA).

The procedure as in example 2 was followed, except that gelatin was replaced with poly(vinyl alcohol).

The porogenic agent A was PMMA microspheres with a diameter between 100 and 300 μm. These microspheres represented 70 vol % of the total volume of the mixture introduced into the mold.

Solvent S1 was water and was heated to 80° C.
Solvent S was acetone.

The composition of the bioactive glass was 75% $SiO_2$-25% CaO, by weight, relative to the total weight of the bioactive glass, and the composition of the final implant material obtained was 30% bioactive glass-70% poly(vinyl alcohol).

Figure 18:
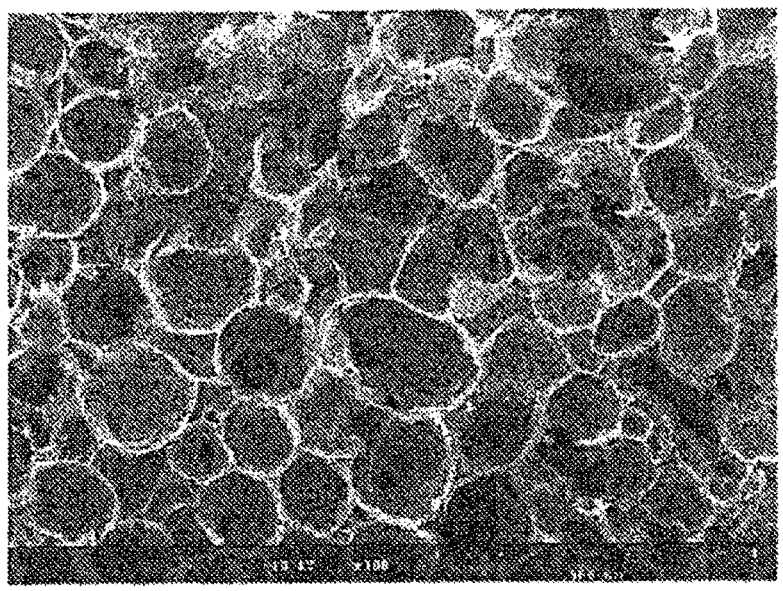

As can be seen in FIG. 18, this implant material has more than 80% by number of spherical pores, all of them having at least one interconnection with at least one other pore.

EXAMPLE 11

Manufacture of an implant material according to the invention with a matrix of hybrid material of class I in which the biodegradable polymer P is carrageenan.

The procedure as in example 2 was followed, except that gelatin was replaced with carrageenan.

The composition of the bioactive glass was 75% $SiO_2$-25% CaO, by weight, relative to the total weight of the bioactive glass, and the final composition of the implant obtained was 30% bioactive glass-70% carrageenan, by weight, relative to the total weight of the implant material.

The porogenic agent A was PMMA microspheres with a diameter between 100 and 300 μm. They represented 60 vol % of the total volume of the mixture introduced into the mold.

Solvent S1 was water heated to 80° C.
Solvent S was acetone.

Figure 19:
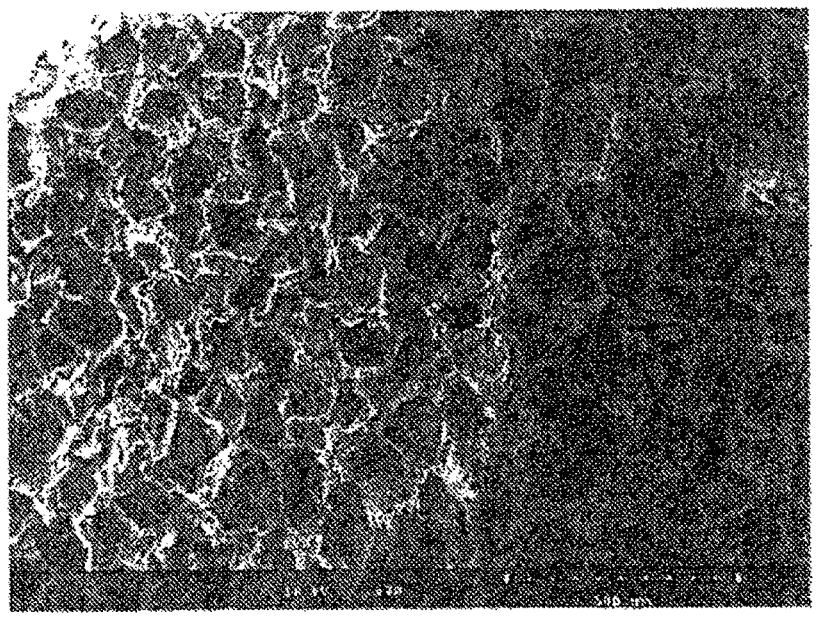

As can be seen in FIG. 19, this implant material has more than 70% by number of spherical pores, all of them interconnected with at least one other pore.

EXAMPLE 12

Manufacture of an implant material according to the invention with a matrix of hybrid material of class I in which the biodegradable polymer P is collagen.

The procedure as in example 2 was followed, except that gelatin was replaced with collagen.

The bioactive glass had the composition 75% $SiO_2$-25% CaO, by weight, relative to the total weight of the bioactive glass, and the implant material obtained had the composition 30% bioactive glass-70% collagen, by weight, relative to the total weight of the implant material obtained.

The porogenic agent A was PMMA microspheres with a diameter between 100 and 300 μm. They represented 70 vol % of the total volume of the mixture introduced into the mold.

Solvent S1 was an aqueous solution at acid pH, preferably at pH=2.
Solvent S was acetone.

Figure 20:
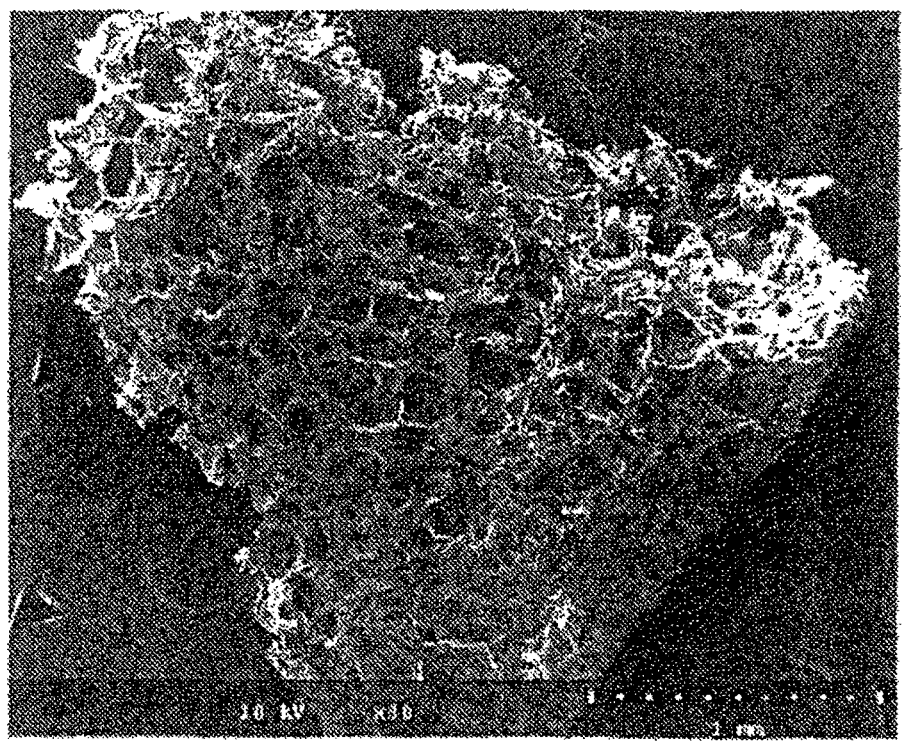

As can be seen in FIG. 20, the implant material obtained has more than 70% by number of spherical pores, all of them having at least one interconnection with at least one other pore.

EXAMPLE 13

Manufacture of an implant material according to the invention with a matrix of hybrid material of class I in which the biodegradable polymer P is hyaluronic acid.

The procedure as in example 2 was followed, except that gelatin was replaced with hyaluronic acid.

The composition of the bioactive glass was 75% $SiO_2$-25% CaO, by weight, relative to the total weight of the bioactive glass, and the composition of the implant material was 30% bioactive glass-70% hyaluronic acid, by weight, relative to the total weight of the implant material obtained.

The porogenic agent A was PMMA microspheres with a diameter between 100 and 300 μm. They represented 60 vol % of the total volume of the mixture introduced into the mold.

Solvent S1 was an acidic aqueous solution (pH=2).
Solvent S was acetone.

Figure 21:
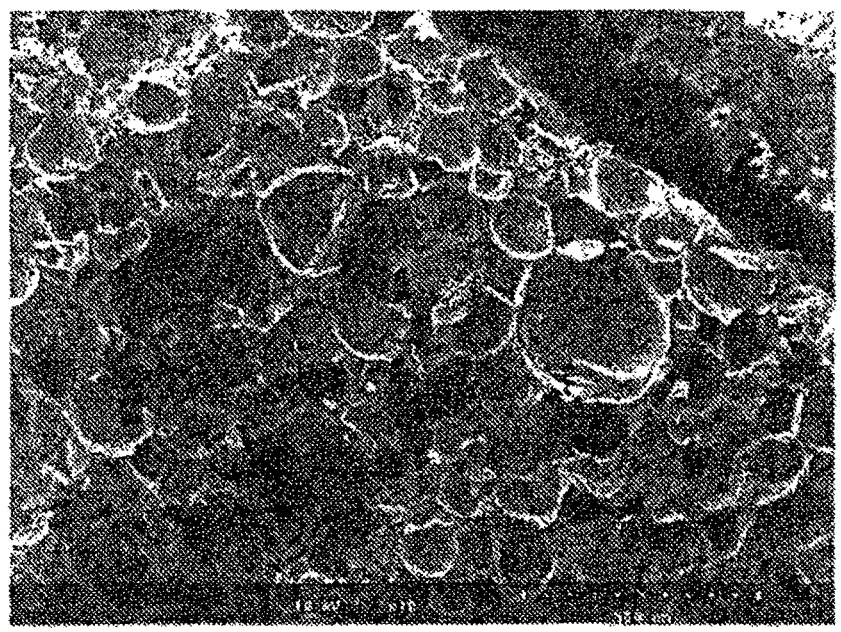

As can be seen in FIG. 21, the implant material obtained has more than 70% by number of spherical pores, all of them having at least one interconnection with at least one other pore.

EXAMPLE 14

Manufacture of an implant material according to the invention with a matrix of hybrid material of class I in which the biodegradable polymer P is poly(caprolactone).

The procedure as in example 2 was followed, except that gelatin was replaced with poly(caprolactone).

The composition of the bioactive glass was 75% $SiO_2$-25% CaO, by weight, relative to the total weight of the bioactive glass, and the implant material obtained had the composition 30% bioactive glass-70% poly(caprolactone), by weight, relative to the total weight of the implant material.

The porogenic agent A was paraffin beads with a diameter between 200 and 400 μm. They represented 70 vol % of the total volume of the mixture introduced into the mold.

Solvent S1 was chloroform.
Solvent S was cyclohexane.

Figure 22:
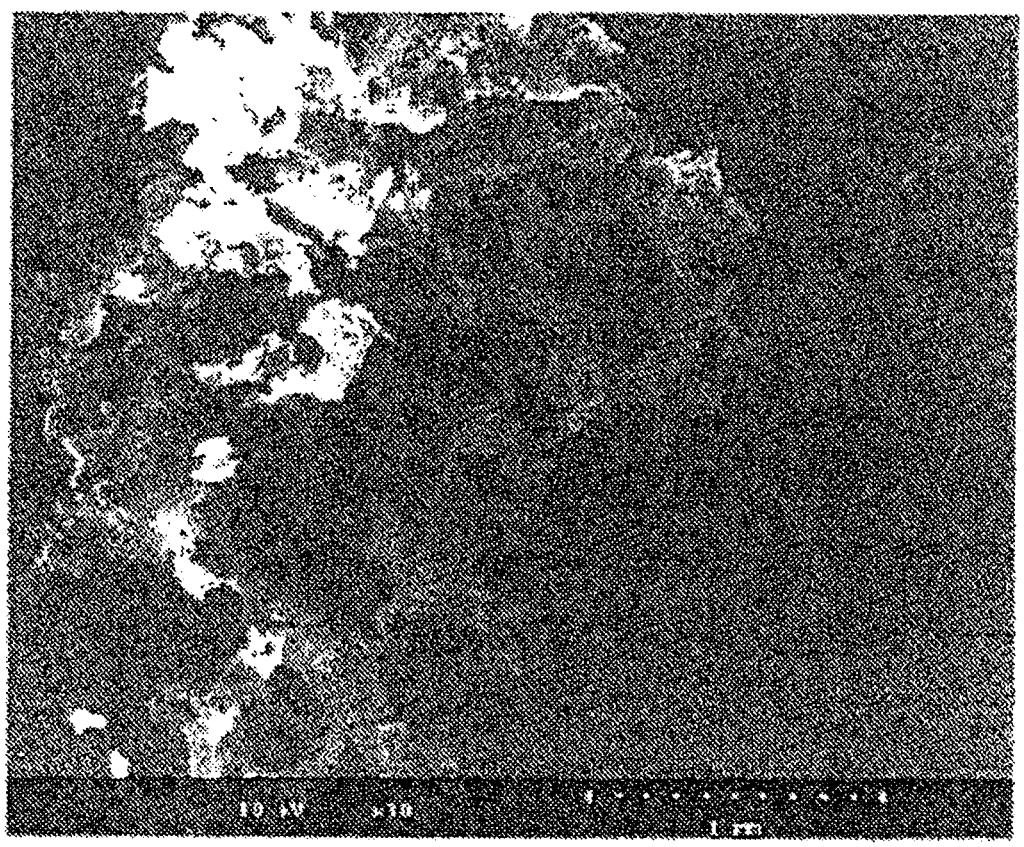

As can be seen in FIG. 22, the implant material obtained has more than 70% by number of spherical pores.

As can also be seen in FIG. 22, at least 70% by number of these pores have at least one interconnection with at least one other pore.

EXAMPLE 15

Manufacture of an implant material according to the invention with a matrix of hybrid material of class I in which the biodegradable polymer P is dextran.

The procedure as in example 2 was followed, except that dextran was used in place of gelatin.

The implant material obtained has more than 90% by number of spherical pores, all of them having at least one interconnection with at least one other pore.

The composition of the bioactive glass was 75% $SiO_2$-25% CaO, by weight.

The porogenic agent A was PMMA beads with a diameter between 100 and 300 µm. They represented 70 vol % of the total volume of the mixture introduced into the mold.

Solvent S1 was an acidic aqueous solution (pH=2).

Solvent S was acetone.

The implant material had the composition 70 wt % dextran-30 wt % bioactive glass.

EXAMPLE 16

Manufacture of an implant material according to the invention with a matrix of hybrid material in which the bioactive glass is a glass doped with strontium.

The procedure as in example 2 was followed, except that a strontium alkoxide (for example strontium isopropoxide) was added to the precursors of silicon and calcium to obtain a bioactive glass having the composition by weight 75% $SiO_2$-20% CaO-5% SrO.

Figure 14A:
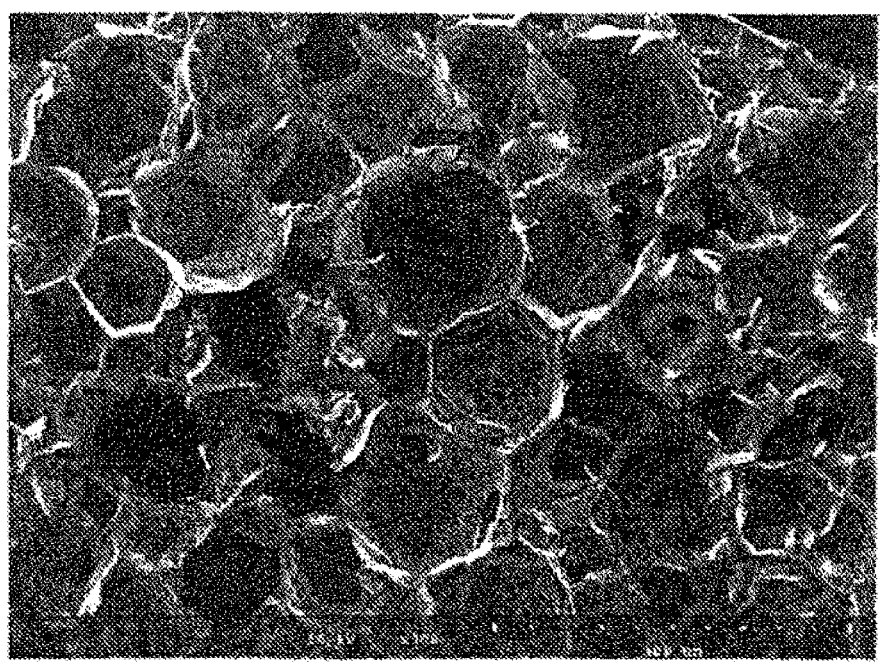

As can be seen in FIG. 14A, the implant material obtained has more than 70% by number of spherical pores having at least one interconnection with another pore.

Figure 14B:
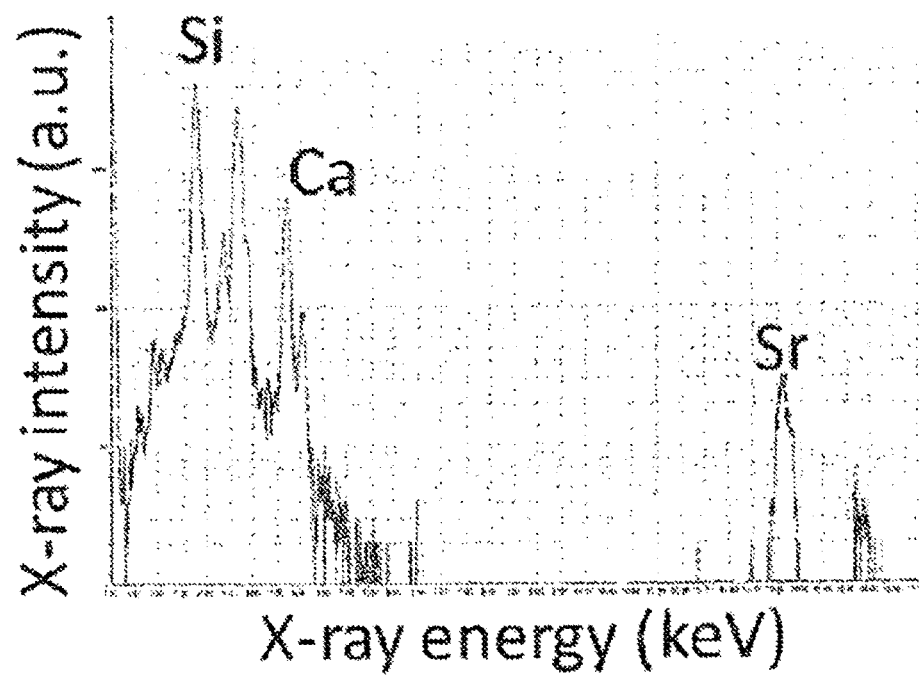

It is made up of a hybrid material of class II in which the bioactive glass has the composition by weight 75% $SiO_2$-20% CaO-5% SrO, as can be seen in FIG. 14B, and represents 30 wt % of the total weight of the material, the remaining 70 wt % being gelatin.

Characterization of the Sphericity of the Macropores Obtained

The synthesis route proposed makes it possible to obtain spherical pores. In fact, measuring two perpendicular diameters for each pore, the ratio of the smallest diameter to the largest diameter is on average 0.9±0.1.

Thus, it can clearly be seen that thanks to the methods of the invention, implants having all the properties of porosity, in terms of pore sizes, sphericity of these pores, distribution of this pore size over a very wide range between 100 and 900 µm, preferably between 200 and 800 µm inclusive, with a difference between the diameter of the smallest or the largest sphere being at most 70%, preferably at most 50%, more preferably at most 30%, relative to the arithmetic mean diameter of the set of spheres of the implant, can be obtained, in conjunction with interconnections between pores for which the smallest dimension is between 25 and 250 micrometers inclusive, which had never been obtained previously.

The invention claimed is:

1. A method for manufacturing an implant made of a hybrid material for filling bone defects, for bone regeneration, and for bone tissue engineering, comprising the following successive steps:
   a) selecting a bioactive glass M based on $SiO_2$ and CaO, optionally containing $P_2O_5$ and/or optionally doped with strontium,
   b) selecting a biodegradable polymer P that is soluble in at least one solvent S1 and insoluble in at least one solvent S different from the solvent S1,
   c) selecting microspheres of a porogenic agent A having diameters and sizes corresponding to the desired diameters and sizes of the pores in the material constituting the implant to be manufactured, this porogenic agent A being:
      a polymer insoluble in the at least one solvent S1 and soluble in the at least one solvent S,
      the at least one solvent S in which the material of the biodegradable polymer P is insoluble and the at least one solvent S in which the material of the porogenic agent A is soluble being identical,
   d) introducing the microspheres of the porogenic agent A into a mold having the required shape and size for the implant, these microspheres forming a compact stack corresponding to the shape and size of the pores to be obtained in the implant material, and representing at least 60 vol % relative to the total volume of the mixture of porogenic agent A-biodegradable polymer P-alkoxide precursors of the bioactive glass M,
   e) adding the biodegradable polymer P to the alkoxide precursors of at least $SiO_2$ and CaO of the bioactive glass M, wherein the alkoxide precursor of CaO is calcium ethoxide,
   f) putting the mixture obtained in step e) into the mold,
   g) gelling the mixture contained in the mold after step f),
   h) removing the mixture obtained in step g) from the mold,
   i) removing the microspheres of porogenic agent A by washing with the solvent S, and
   j) crosslinking of the mixture obtained in step i).

2. The method as claimed in claim 1, wherein step e) and/or step f) are carried out before step d).

3. The method as claimed in claim 1, wherein steps d) and e) and f) are carried out simultaneously.

4. The method as claimed in claim 1, wherein the biodegradable polymer P is selected from:
   biodegradable polymers that are soluble in at least one solvent S1 and insoluble in at least one solvent S selected from:
   bioabsorbable polysaccharides,
   bioabsorbable polyesters,
   biodegradable synthetic polymers,
   proteins,
   wherein the material of the porogenic agent A is selected from biodegradable polymers that are insoluble in the at least one solvent S1 and soluble in the at least one solvent S, and
   the material of the porogenic agent A being different from the biodegradable polymer P.

5. The method as claimed in claim 1, wherein the weight ratio biodegradable polymer P/bioactive glass M is between 20/80 and 80/20, inclusive.

6. The method as claimed in claim 1, wherein the bioactive glass M is a glass based on $SiO_2$ and CaO, the biodegradable polymer P is gelatin, the material of the microspheres of porogenic agent A is polymethyl methacrylate and the solvent S is acetone.

7. The method as claimed in claim 1, further comprising, in step f), a step of introducing a coupling agent.

8. The method as claimed in claim 1, comprising after step d), and before step e), a step of enlarging the interconnections (4), by infiltration of a solvent S of the material of the porogenic agent A, into the stack of the microspheres of porogenic agent A and/or by heating this stack.

9. The method as claimed in claim 1 wherein, in step d), the microspheres of the porogenic agent A represent at least 70 vol % relative to the total volume of the mixture of porogenic agent A-biodegradable polymer P-alkoxide precursors of the bioactive glass M.

10. The method as claimed in claim 4 wherein:
the bioabsorbable polysaccharides are selected from the group consisting of dextran, hyaluronic acid, agar, chitosan, alginic acid, sodium or potassium alginate, galactomannan, carrageenan, and pectin,
the bioabsorbable polyesters are polyvinyl alcohol or poly(lactic acid),
the biodegradable synthetic polymers are a polyethylene glycol, or poly(caprolactone),
the proteins are gelatin or collagen.

11. The method as claimed in claim 4 wherein the material of the porogenic agent A is selected from the group consisting of C1 to C4 polyalkyl methacrylates, polymethyl methacrylate or polybutyl methacrylate, polyurethane, polyglycolic acid, copolymers of lactic-coglycolic acids, polycaprolactone, polypropylene fumarate, paraffin and naphthalene, and acrylonitrile butadiene styrene (ABS).

12. The method as claimed in claim 7 wherein the coupling agent is an organoalkoxysilane compound.

13. The method as claimed in claim 12 wherein the organoalkoxysilane compound is 3-glycidoxypropyltrimethoxysilane (GPMS) or 3-glycidoxypropyltriethoxysilane (GPTES).

\* \* \* \* \*